US006815091B2

(12) United States Patent
Takiguchi et al.

(10) Patent No.: US 6,815,091 B2
(45) Date of Patent: Nov. 9, 2004

(54) LUMINESCENCE DEVICE, DISPLAY APPARATUS AND METAL COORDINATION COMPOUND

(75) Inventors: Takao Takiguchi, Tokyo (JP); Hidemasa Mizutani, Sagamihara (JP); Shinjiro Okada, Isehara (JP); Akira Tsuboyama, Sagamihara (JP); Seishi Miura, Sagamihara (JP); Takashi Moriyama, Kawasaki (JP); Satoshi Igawa, Fujisawa (JP); Jun Kamatani, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/961,075

(22) Filed: Sep. 24, 2001

(65) Prior Publication Data

US 2002/0064681 A1 May 30, 2002

(30) Foreign Application Priority Data

| | | |
|---|---|---|
| Sep. 26, 2000 | (JP) | 2000-292492 |
| Sep. 26, 2000 | (JP) | 2000-292493 |
| Nov. 27, 2000 | (JP) | 2000-358741 |
| Nov. 27, 2000 | (JP) | 2000-358742 |
| Aug. 27, 2001 | (JP) | 2001-255537 |
| Sep. 19, 2001 | (JP) | 2001-284599 |

(51) Int. Cl.[7] ........ H05B 33/14; C09K 11/06; C07D 213/02

(52) U.S. Cl. ........ 428/690; 428/917; 313/504; 546/4

(58) Field of Search ........ 428/690, 917; 313/504; 252/301.16; 546/2, 4

(56) References Cited

U.S. PATENT DOCUMENTS

| | | | | |
|---|---|---|---|---|
| 5,150,006 A | * | 9/1992 | Van Slyke et al. | 313/504 |
| 5,484,922 A | * | 1/1996 | Moore et al. | 546/7 |
| 5,698,858 A | | 12/1997 | Börner | 250/484.2 |
| 2001/0019782 A1 | * | 9/2001 | Igarashi et al. | 428/690 |
| 2002/0034656 A1 | * | 3/2002 | Thompson et al. | 428/690 |
| 2002/0121638 A1 | * | 9/2002 | Grushin et al. | 257/40 |

FOREIGN PATENT DOCUMENTS

| | | |
|---|---|---|
| EP | 1 175 128 A2 | 1/2002 |
| JP | 8-319482 | 12/1996 |
| JP | 11-256148 | 9/1999 |
| JP | 11-329739 | 11/1999 |
| WO | WO 02/02714 A2 | 1/2002 |
| WO | WO 02/15645 A1 | 2/2002 |

OTHER PUBLICATIONS

Peter I. Djurovich et al., "Ir(III) Cyclometalated Complexes as Efficient Phosphoresc nt Emitters in Polymer Blend and Organic LEDs," 41(1) *Polymer Preprints* 770–771, Mar. 2000.

C.H. Chen et al., "Recent Developments in Molecular Organic Electroluminescent Materials," 125 *Macromol. Symp.* 1–48 (1997), no month.

D.F. O'Brien et al., "Improved Energy Transfer in Electrophosphorescent Devices," 74(3) *Appl. Phys. Lett.* 442–444, Jan. 1999.

M.A. Baldo et al., "Very High–Efficiency Green Organic Light–Emitting Devices Based on Electrophosphorescence," 75(1) *Appl. Phys. Lett.* 4–6, Jul. 1999.

Moon–Jay Yang et al., "Organic Light–Emitting Devices Used New Iridium Complexes as Triplet–State Emitter," *Preprint for the 61$^{st}$ Academical Lecture of the Applied Physics Society of Japan,* v 3. p. 1117, 6p–ZH–1 (2000), no month.

Sergey Lamansky et al., "Molecularly Doped Polymer Light Emitting Diodes Utilizing Phosphorescent Pt(II) and Ir(III) Dopants," 2 *Organic Electronics* 53–62 (Mar. 2001).

Vladimir V. Grushin et al., "New, Efficient Electroluminescent Materials Based on Organomettalic Ir Complexes," *Chem. Commun.* 1494–1495 (Jul. 23, 2001).

(List continued on next page.)

*Primary Examiner*—Marie Yamnitzky
(74) *Attorney, Agent, or Firm*—Fitzpatrick, Cella, Harper & Scinto

(57) ABSTRACT

A luminescence device comprising a pair of electrodes and an organic compound layer disposed therebetween. The layer contains a metal coordination compound represented by the following formula (1):

(1)

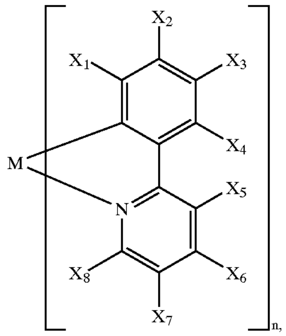

wherein M is Ir, Rh or Pd; n is 2 or 3; and $X_1$ to $X_8$ is, independently, a hydrogen atom or a substituent selected from the group consisting of a halogen atom; a nitro group; a trifluoromethyl group; a trialkylsilyl group having three linear or branched alkyl groups each independently having 1–8 carbon atoms; and a linear or branched alkyl group having 2–20 carbon atoms capable of including one or at least two non-neighboring methylene groups which can be replaced with —O—, —S—, —C(O)—, —C(O)—O—, —O—C(O)—, —CH=CH— or —C≡C— and capable of including hydrogen atom which can be replaced with fluorine atom.

10 Claims, 2 Drawing Sheets

OTHER PUBLICATIONS

Alan Ford et al., "Regioselectivity in Metallation Reactions of 2'–(2–naphthyl)pyridine: 1'–versus 3'–reactivity in Mercuration and Palladation Reactions. Crystal Structure of Chloro(pyridine) [2–(2'–pyridinyl)naphthyl–$C^3$,N]palladium," 493 *J. Organometal. Chem.* 215–220 (1995).

Chihaya Adachi et al., "High–Efficiency Organic Electrophosphorescent Devices with Tris(2– phenylpyridine)iridium Doped into Electron–Transporting Materials," 77(6) *Appl. Phys. Lett.* 904–906 (Aug. 7, 2000).

* cited by examiner

LUMINESCENCE DEVICE, DISPLAY APPARATUS AND METAL COORDINATION COMPOUND

FIELD OF THE INVENTION AND RELATED ART

The present invention relates to a luminescence device, a metal coordination compound therefor and a display apparatus including the luminescence device. More specifically, the present invention relates to an organic (electro-) luminescence device employing a metal coordination compound having a formula (1) or (2) appearing hereinafter as a luminescence material, the metal coordination compound adapted for use in the luminescence device, and a display apparatus using the luminescence device.

An organic electroluminescence (EL) device has been extensively studied as a luminescence device with a high responsiveness and high efficiency.

The organic EL device generally has a sectional structure as shown in FIG. 1A or 1B (e.g., as described in "Macromol. Symp.", 125, pp. 1–48 (1997)).

Referring to the figures, the EL device generally has a structure including a transparent substrate 15, a transparent electrode 14 disposed on the transparent substrate 15, a metal electrode 11 disposed opposite to the transparent electrode 14, and a plurality of organic (compound) layers disposed between the transparent electrode 14 and the metal electrode 11.

Referring to FIG. 1, the EL device in this embodiment has two organic layers including a luminescence layer 12 and a hole transport layer 13.

The transparent electrode 14 may be formed of a film of ITO (indium tin oxide) having a larger work function to ensure a good hole injection performance into the hole transport layer. On the other hand, the metal electrode 11 may be formed of a layer of aluminum, magnesium, alloys thereof, etc., having a smaller work function to ensure a good electron injection performance into the organic layer (s).

These (transparent and metal) electrodes 14 and 11 may be formed in a thickness of 50–200 nm.

The luminescence layer 12 may be formed of, e.g., aluminum quinolinol complex (representative example thereof may include Alq3 described hereinafter) having an electron transporting characteristic and a luminescent characteristic. The hole transport layer 13 may be formed of, e.g., triphenyldiamine derivative (representative example thereof may include α-NPD described hereinafter) having an electron donating characteristic.

The above-described EL device exhibits a rectification characteristic, so that when an electric field is applied between the metal electrode 11 as a cathode and the transparent electrode 14 as an anode, electrons are injected from the metal electrode 11 into the luminescence layer 12 and holes are injected from the transparent electrodes 14.

The thus-injected holes and electrons are recombined within the luminescence layer 12 to produce excitons, thus causing luminescence. At that time, the hole transport layer 13 functions as an electron-blocking layer to increase a recombination efficiency at the boundary between the luminescence layer 12 and the hole transport layer 13, thus enhancing a luminescence efficiency.

Referring to FIG. 1B, in addition to the layers shown in FIG. 1A, an electron transport layer 16 is disposed between the metal electrode 11 and the luminescence layer 12, whereby an effective carrier blocking performance can be ensured by separating functions of luminescence, electron transport and hole transport, thus allowing effective luminescence.

The electron transport layer 16 may be formed of, e.g., oxadiazole derivatives.

In ordinary organic EL devices, fluorescence caused during a transition of luminescent center molecule from a singlet excited state to a ground state is used as luminescence.

On the other hand, not the above fluorescence (luminescence) via singlet exciton, phosphorescence (luminescence) via triplet exciton has been studied for use in organic EL device as described in, e.g., "Improved energy transfer in electrophosphorescent device" (D. F. O'Brien et al., Applied Physics Letters, Vol. 74, No. 3, pp. 442–444 (1999)) and "Very high-efficiency green organic light-emitting devices based on electrophosphorescence" (M. A. Baldo et al., Applied Physics Letters, Vol. 75, No. 1, pp. 4–6 (1999)).

The EL devices shown in these documents may generally have a sectional structure shown in FIG. 1C.

Referring to FIG. 1C, four organic layers including a hole transfer layer 13, a luminescence layer 12, an exciton diffusion-prevention layer 17, and an electron transport layer 16 are successively formed in this order on the transparent electrode (anode) 14.

In the above documents, higher efficiencies have been achieved by using four organic layers including a hole transport layer 13 of α-NPD (shown below), an electron transport layer 16 of Alq3 (shown below), an exciton diffusion-prevention layer 17 of BPC (shown below), and a luminescence layer 12 of a mixture of CPB (shown below) as a host material with $Ir(ppy)_3$ (shown below) or PtOEP (shown below) as a guest phosphorescence material doped into CBP at a concentration of ca. 6 wt. %.

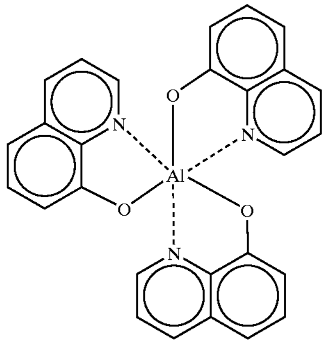

Alq3

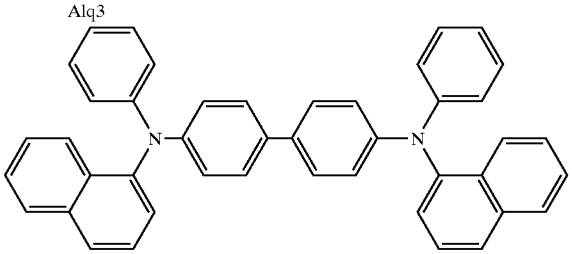

α-NPD

-continued

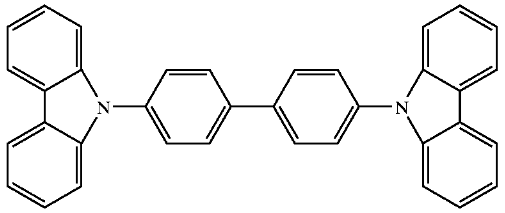

CBP

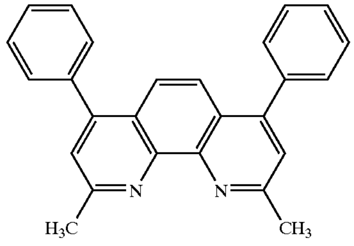

BCP

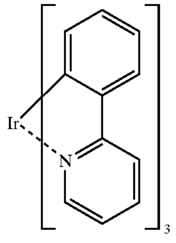

$Ir(ppy)_3$

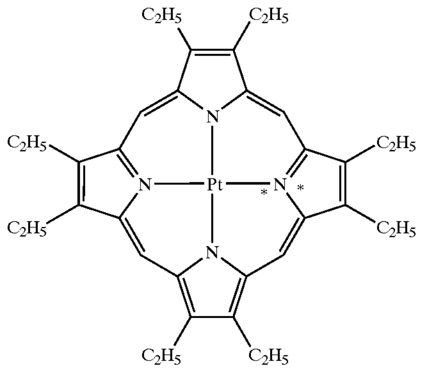

PtOEP

Alq3: tris(8-hydroxyquinoline) aluminum (aluminum-quinolinol complex),

α-NPD: N4,N4'-di-naphthalene-1-yl-N4,N4'-diphenyl-biphenyl-4,4'-diamine (4,4'-bis[N-(1-naphthyl)-N-phenyl-amino]biphenyl), CBP: 4,4'-N,N'-dicarbazole-biphenyl, BCP: 2,9-dimethyl-4,7-diphenyl-1,10-phenanthroline, $Ir(ppy)_3$: fac tris(2-phenylpyridine)iridium (iridium-phenylpyridine complex), and PtEOP: 2,3,7,8,12,13,17,18-octaethyl-21H,23H-porphine platinum (platinum-octaethyl porphine complex).

The phosphorescence (luminescence) material used in the luminescence layer 12 has attracted notice. This is because the phosphorescence material is expected to provide a higher luminescence efficiency in principle.

More specifically, in the case of the phosphorescence material, excitons produced by recombination of carriers comprise singlet excitons and triplet excitons presented in a ratio of 1:3. For this reason, when fluorescence caused during the transition from the singlet excited state to the ground state is utilized, a resultant luminescence efficiency is 25% (as upper limit) based on all the produced excitons in principle.

On the other hand, in the case of utilizing phosphorescence caused during transition from the triplet excited state, a resultant luminescence efficiency is expected to be at least three times that of the case of fluorescence in principle. In addition thereto, if intersystem crossing from the singlet excited state (higher energy level) to the triplet excited state is taken into consideration, the luminescence efficiency of phosphorescence can be expected to be 100% (four times that of fluorescence) in principle.

The use of phosphorescence based on transition from the triplet excited state has also been proposed in, e.g., Japanese Laid-Open Patent Application (JP-A) 11-329739, JP-A 11-256148 and JP-A 8-319482.

An iridium-phenylpyridine complex having a methyl substituent has been described in "Preprint for the 61-st Academical Lecture of the Applied Physics Society of Japan", the third volume, P.1117, 6p-ZH-1 (2000) ("Document 1"). Further, an iridium-phenylpyridine complex having 4-, 5-fluorine substituents (herein, referred to as a "metal coordination compound A" has been described in "Polymer Preprints", 41(1), pp. 770–771 (2000) ("Document 2").

However, the above-mentioned organic EL devices utilizing phosphorescence have accompanied with a problem of luminescent deterioration particularly in an energized state.

The reason for luminescent deterioration has not been clarified as yet but may be attributable to such a phenomenon that the life of triplet exciton is generally longer than that of singlet exciton by at least three digits, so that molecule is placed in a higher-energy state for a long period to cause reaction with ambient substance, formation of exciplex or excimer, change in minute molecular structure, structural change of ambient substance, etc.

Accordingly, the (electro)phosphorescence EL device is expected to provide a higher luminescence efficiency as described above, while the EL device is required to suppress or minimize the luminescent deterioration in energized state.

SUMMARY OF THE INVENTION

An object of the present invention is to provide a luminescence device capable of providing a high-efficiency luminescent state at a high brightness (or luminance) for a long period while minimizing the deterioration in luminescence in energized state.

Herein, although evaluation criteria for "high efficiency" and "high brightness (luminance) for a long period" may vary depending on luminescent performances required for an objective luminescence device (EL device), for example, a luminescence efficiency of at least 1 cd/W based on an inputted current value may be evaluated as "high efficiency". Further, a luminance half-life of, e.g., at least 500 hours at the time of luminescence at an initial luminance of 100 $cd/m^2$ may be evaluated as "high brightness (luminance) for a long period" or a smaller luminance deterioration in energized state.

Another object of the present invention is to provide a metal coordination compound as a material suitable for an organic layer for the luminescence device.

According to the present invention, there is provided a luminescence device, comprising: an organic compound layer comprising a metal coordination compound represented by the following formula (1):

(1)

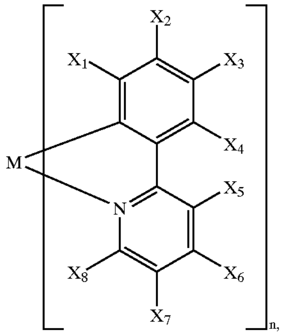

wherein M denotes Ir, Rh or Pd; n is 2 or 3; and X1 to X8 independently denote hydrogen atom or a substituent selected from the group consisting of halogen atom; nitro group; trifluoromethyl group; trialkylsilyl group having three linear or branched alkyl groups each independently having 1–8 carbon atoms; and a linear or branched alkyl group having 2–20 carbon atoms capable of including one or at least two non-neighboring methylene groups which can be replaced with —O—, —S—, —CO—, —CO—O—, —O—CO—, —CH═CH— or —C≡C— and capable of including hydrogen atom which can be replaced with fluorine atom; with the proviso that at least one of X1 to X8 is a substituent other than hydrogen atom, and X2 and X3 cannot be fluorine atom at the same time.

According to the present invention, there is also provided a metal coordination compound, adapted for use in a luminescence device, represented by the following formula (1):

(1)

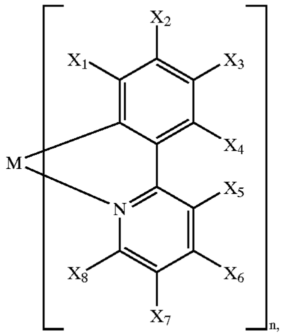

wherein M denotes Ir, Rh or Pd; n is 2 or 3; and X1 to X8 independently denote hydrogen atom or a substituent selected from the group consisting of halogen atom; nitro group; trifluoromethyl group trialkylsilyl group having three linear or branched alkyl groups each independently having 1–8 carbon atoms; and a linear or branched alkyl group having 2–20 carbon atoms capable of including one or at least two non-neighboring methylene groups which can be replaced with —O—, —S—, —CO—, —CO—O—, —O—CO—, —CH═CH— or —C≡C— and capable of including hydrogen atom which can be replaced with fluorine atom; with the proviso that at least one of X1 to X8 is a substituent other than hydrogen atom, and X2 and X3 cannot be fluorine atom at the same time.

The present invention provides a luminescence device, comprising: an organic compound layer comprising a metal coordination compound represented by the following formula (2):

(2)

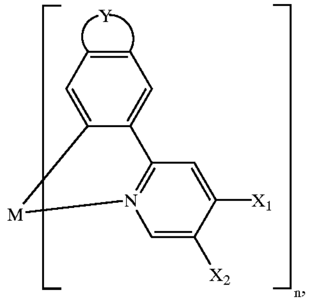

wherein M denotes Ir, Rh or Pd; n is 2 or 3; Y denotes an alkylene group having 2–4 carbon atoms capable of including one or at least two non-neighboring methylene groups which can be replaced with —O—, —S— or —CO— and capable of including hydrogen atom which can be replaced with a linear or branched alkyl group having 1–10 carbon atoms; and X1 and X2 independently denote hydrogen atom; halogen atom; nitro group; trialkylsilyl group having 1–8 carbon atoms; or a linear or branched alkyl group having 1–20 carbon atoms capable of including one or at least two non-neighboring methylene groups which can be replaced with —O—, —S—, —CO—, —CO—O—, —O—CO—, —CH═CH— or —C≡C— and capable of including hydrogen atom which can be replaced with fluorine atom.

The present invention also provides a metal coordination compound, adapted for use in a luminescence device, represented by the following formula (2):

(2)

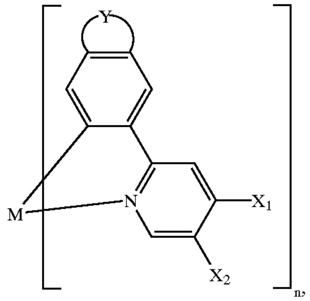

wherein M denotes Ir, Rh or Pd; n is 2 or 3; Y denotes an alkylene group having 2–4 carbon atoms capable of including one or at least two non-neighboring methylene groups which can be replaced with —O—, —S— or —CO— and capable of including hydrogen atom which can be replaced with a linear or branched alkyl group having 1–10 carbon atoms; and X1 and X2 independently denote hydrogen atom; halogen atom; nitro group; trialkylsilyl group having 1–8 carbon atoms; or a linear or branched alkyl group having 1–20 carbon atoms capable of including one or at least two non-neighboring methylene groups which can be replaced with —O—, —S—, —CO—, —CO—O—, —O—CO—, —CH═CH— or —C≡C— and capable of including hydrogen atom which can be replaced with fluorine atom.

The present invention further provides a display apparatus including the above-mentioned luminescence device and drive means for driving the luminescence device.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1A:
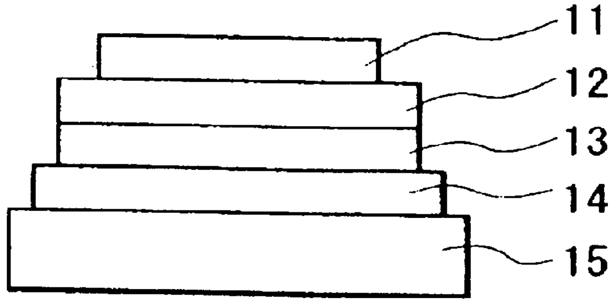
FIGS. 1A, 1B and 1C are respectively a schematic sectional view of a layer structure of a luminescence device.

In the case where a luminescence layer for an organic EL device is formed of a carrier transporting host material and a phosphorescent guest material, a process of emission of light (phosphorescence) may generally involve the following steps:

(1) transport of electron and hole within a luminescence layer, (2) formation of exciton of the host material, (3) transmission of excited energy between host material molecules, (4) transmission of excited energy from the host material molecule to the guest material molecule, (5) formation of triplet exciton of the guest material, and (6) emission of light (phosphorescence) caused during transition from the triplet excited state to the ground state of the guest material.

In the above steps, desired energy transmission and luminescence may generally be caused based on various quenching and competition.

In order to improve a luminescence efficiency of the EL device, a luminescence center material per se is required to provide a higher yield of luminescence quantum. In addition thereto, an efficient energy transfer between host material molecules and/or between host material molecule and guest material molecule is also an important factor.

Further, the above-described luminescent deterioration in energized state may presumably relate to the luminescent center material per se or an environmental change thereof by its ambient molecular structure.

For this reason, our research group has extensively investigated an effect of use of various metal coordination compounds as the luminescent center material and as a result, has found that the metal coordination compound represented by the above-mentioned formula (1) or (2) allows a high-efficiency luminescence with a high brightness (luminance) for a long period (i.e., a decreased luminescent deterioration in energized state).

The metal coordination compound of formula (1) may preferably have substituents X1 to X8 in which at least two of X1 to X8 are substituents other than hydrogen atom. Further, in the formula (1), at least one of X5 to X8 may preferably be a substituent other than hydrogen atom and/or at least two of X1 to X4 may preferably be substituents other than hydrogen atom.

The metal coordination compound represented by the formulas (1) causes phosphorescence (luminescence) and is assumed to have a lowest excited state comprising a triplet excited state liable to cause metal-to-ligand charge transfer (MLCT* state). The phosphorescent emission of light (phosphorescence) is produced during the transition from the MLCT* state to the ground state.

The metal coordination compound of formula (1) according to the present invention has been found to provide a higher phosphorescence yield of 0.1–0.9 and a shorter phosphorescence life of 1–60 μsec.

A phosphorescence yield (P(m)) is obtained based on the following equation:

$$P(m)/P(s)=(S(m)/S(s))\times(A(s)/A(m)),\ \text{wherein}$$

represents a phosphorescence yield of an (unknown) objective luminescent material, P(s) represents a known (standard) phosphorescence yield of standard luminescent material ($Ir(ppy)_3$), S(m) represents an integrated intensity of (photo-)excited emission spectrum of the objective material, S(s) represents a known integrated intensity of the standard material, A(m) represents an absorption spectrum of an excited light wavelength of the objective material, and A(s) represents a known absorption spectrum of the standard material.

The shorter phosphorescence life is necessary to provide a resultant EL device with a higher luminescence efficiency. This is because the longer phosphorescence life increases molecules placed in their triplet excited state which is a waiting state for phosphorescence, thus lowering the resultant luminescence efficiency particularly at a higher current density.

Accordingly, the metal coordination compound of formula (1) according to the present invention is a suitable luminescent material for an EL device with a higher phosphorescence yield and a shorter phosphorescence life.

Further, we have found that it is possible to control an emission wavelength of the metal coordination compound of formula (1) by appropriately modifying the substituents X1 to X8 thereof. In this regard, as a result of our investigation on various phosphorescence metal coordination compounds for a blue luminescence material required to have a peak (maximum) emission wavelength of at most 490 nm, we have found that it is very effective to introduce at least one substituent having a Hammett's substituent constant of at least 0.2 into the metal coordination compound of formula (1) in order to provide a shorter peak emission wavelength.

More specifically we investigated a relationship between Hammett's substituent constants σ of substituents X2, X3 and X4 with respect to carbon atom connected to iridium of an iridium complex (metal coordination compound) shown below and peak emission wavelengths $\lambda_{PE}$ in toluene at 25° C.

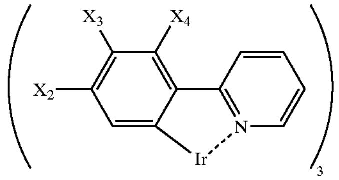

With respect to the Hammett's substituent constant σ, a Hammett's substituent constant σm for meta-position was used for the substituents X2 and X4 and a Hammett's substituent constant σp for para-position was used for the substituent X3. When two or more substituents other than hydrogen atom were present at X2 to X4, a sum of σm and σp was used as a Hammett's substituent constant σ.

In the present invention, specific values of σm and σp described on pages 96–103 (Table 1) of "Correlation between Structure and Activation of Drugs", Chemical Region Extra Edition 122, issued by Nanko-do (Japan) were used as those for X2 to X4. A part of σm and σp described therein is shown in Table 1 below.

TABLE 1

| Substituent | σp | σm |
|---|---|---|
| F | 0.06 | 0.34 |
| Cl | 0.23 | 0.37 |
| $CF_3$ | 0.54 | 0.43 |

For example, a metal coordination compound (Example Compound No. (121) appearing hereinafter, X2=F, X3=$CF_3$, X4=H) has a Hammett's substituent constant σ=0.34+0.54=0.88. In a similar manner, Hammett's substituent constants σ of several metal coordination compounds (Ex. Comp. Nos. (1), (32), (122) and (111) described later and the metal coordination compound A described in the above-mentioned Document 2) are calculated and shown in Table 2 below together with corresponding peak emission wavelength $\lambda_{PE}$ in toluene at 25° C. The results of Table 2 are also shown in FIG. 2.

TABLE 2

| Compound | σ | $\lambda_{PE}$ (nm) |
|---|---|---|
| Ex. Comp. No. (1) | 0.06 | 522 |
| Metal coordination compound A | 0.40 | 505 |
| Ex. Comp. No. (32) | 0.54 | 487 |
| Ex. Comp. No. (122) | 0.68 | 471 |
| Ex. Comp. No. (121) | 0.88 | 466 |
| Ex. Comp. No. (111) | 0.91 | 479 |

Figure 2:
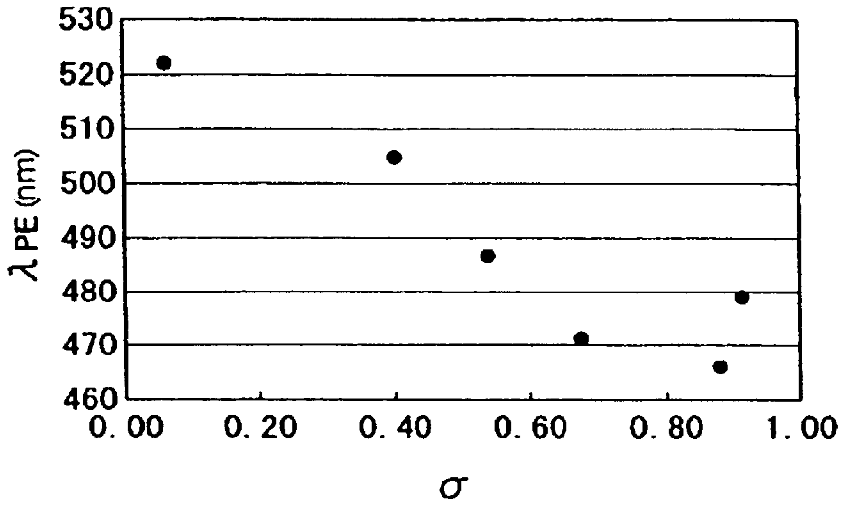
FIG. 2 is a graph showing a relationship between a Hammett's substitution constant σ and a peak (maximum) emission wavelength $\lambda_{PE}$.

As apparent from Table 2 and FIG. 2, introduction of substituent(s) having a larger Hammett's substituent constant is very effective to shorten the peak emission wavelength. Specifically, the metal coordination compound having the sum of peak emission wavelengths of at least 0.41, particularly at least 0.50 is suitable as the blue luminescent material. A similar effect can be expected also for metal coordination compounds other than the metal coordination compound of formula (1) of the present invention.

As described above, the metal coordination compound of formula (1) is a suitable luminescent material for the EL device.

Further, as shown in Examples appearing hereinafter, it has been substantiated that the metal coordination compound of formula (1) of the present invention has an excellent stability in a continuous energization test.

This may be attributable to introduction of particular substituents (X1 to X8) allowing control of intermolecular interaction with a host luminescent material (e.g., CBP described above) and suppression of formation of associated exciton leading to thermal quenching, thus minimizing quenching to improve device characteristics.

In this regard, the methyl group of methyl-substituted iridium-phenylpyrimidine complex described in the above-mentioned Document 1 has a smaller bulkiness than ethyl group and methoxy group and a smaller electronic effect than halogen atom, trifluoromethyl group and methoxy group. As a result, the effect of controlling intermolecular interaction in the present invention cannot be expected.

Further, compared with 4-, 5-fluorine (substituted) iridium-phenylpyrimidine complex (metal coordination compound A) described in the above-mentioned Document 2, it has been substantiated that a luminescence device using the metal coordination compound of formula (1) according to the present invention has a higher durability, i.e., a higher luminance stability for a long period, shown in Examples described later.

Further, in the case of phosphorescent (luminescent) material, luminescent characteristics are largely affected by its molecular environment. On the other hand, principal characteristics of the fluorescent material are studied based on photoluminescence.

For this reason, results of photoluminescence of the phosphorescent material do not reflect luminescent characteristics of the resultant EL device in many cases since the luminescent characteristics in the case of the phosphorescent material depend on a magnitude of polarity of ambient host material molecules, ambient temperature, presence state of the material (e.g., solid state or liquid state, etc. Accordingly, different from the fluorescent material, it is generally difficult to expect the resultant EL characteristics for the phosphorescent material by simply removing a part of characteristics from photoluminescence results.

Next, the metal coordination compound of formula (2) according to the present invention will be described.

The metal coordination compound of formula (2) may preferably have hydrogen atom(s) as at least one of X1 and X2 in the formula (2).

Similarly as the metal coordination compound of formula (1), the metal coordination compound of formula (2) also causes phosphorescence (luminescence) and is assumed to have a lowest excited state comprising a triplet excited state liable to cause metal-to-ligand charge transfer (MLCT* state). The phosphorescent emission of light (phosphorescence) is produced during the transition from the MLCT* state to the ground state.

The metal coordination compound according to the present invention has been found to provide a higher phosphorescence yield of 0.15–0.9 and a shorter phosphorescence life of 1–40 μsec, as a result of a luminescence test based on photo-luminescence by photo-excitation.

The shorter phosphorescence life is necessary to provide a resultant EL device with a higher luminescence efficiency. This is because the longer phosphorescence life increases molecules placed in their triplet excited state which is a waiting state for phosphorescence, thus lowering the resultant luminescence efficiency particularly at a higher current density.

Accordingly, the metal coordination compound of formula (2) according to the present invention is a suitable luminescent material for an EL device with a higher phosphorescence yield and a shorter phosphorescence life.

Further, by appropriately modifying the alkylene group Y and/or the substituents X1 and X2, emission wavelength control can be expected for the resultant metal coordination compound of formula (2).

As described above, the metal coordination compound of formula (2) is a suitable luminescent material for the EL device.

Further, as shown in Examples appearing hereinafter, it has been substantiated that the metal coordination compound of formula (2) of the present invention has an excellent stability in a continuous energization test.

This may be attributable to introduction of particular alkylene group and/or substituents (Y, X1, X2) allowing control of intermolecular interaction with a host luminescent material (e.g., CBP described above) and suppression of formation of associated exciton leading to thermal quenching, thus minimizing quenching to improve device characteristics.

The luminescence device (EL) device according to the present invention employs the above-mentioned metal coordination compound in an organic layer, particularly a luminescence layer.

Specifically, the luminescence device may preferably include the organic layer comprising the metal coordination compound of formula (1) or formula (2) between a pair of oppositely disposed electrodes comprising a transparent electrode (anode) and a metal electrode (cathode) which are supplied with a voltage to cause luminescence, thus constituting an electric-field luminescence device.

Figure 1B:
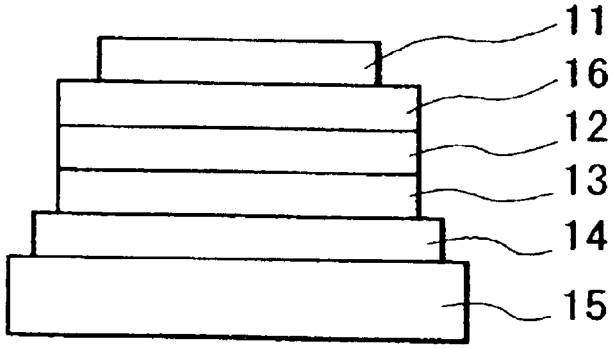
Figure 1C:
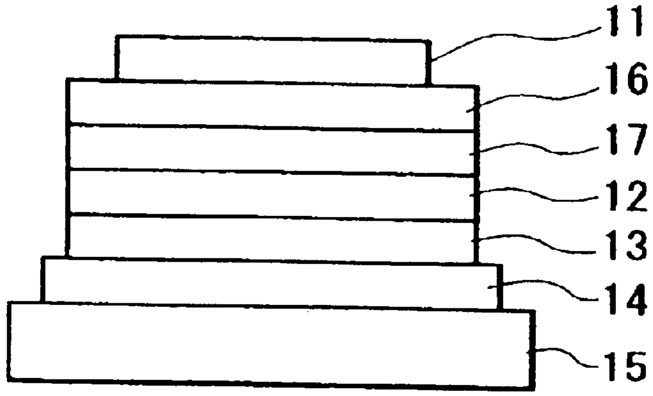

The luminescence device of the present invention has a layer structure shown in FIGS. 1A to 1C as specifically described above.

By the use of the metal coordination compound of formula (1) or formula (2) of the present invention, the resultant luminescence device has a high luminescence efficiency as described above.

The luminescence device according to the present invention may be applicable to devices required to allow energy saving and high luminance, such as those for display apparatus and illumination apparatus, a light source for printers, and backlight (unit) for a liquid crystal display apparatus. Specifically, in the case of using the luminescence device of the present invention in the display apparatus, it is possible to provide a flat panel display apparatus capable of exhibiting an excellent energy saving performance, a high visibility and a good lightweight property. With respect to the light source, it becomes possible to replace a laser light source of laser beam printer currently used widely with the luminescence device according to the present invention. Further, when the luminescence device of the present invention is arranged in independently addressable arrays as an exposure means for effecting desired exposure of light to a photosensitive drum for forming an image, it becomes possible to considerably reducing the volume (size) of image forming apparatus. With respect to the illumination apparatus and backlight (unit), the resultant apparatus (unit) using the luminescence device of the present invention is expected to have an energy saving effect.

The metal coordination compound of formula (1) may generally be synthesized through the following reaction scheme.

(Iridium Complex)

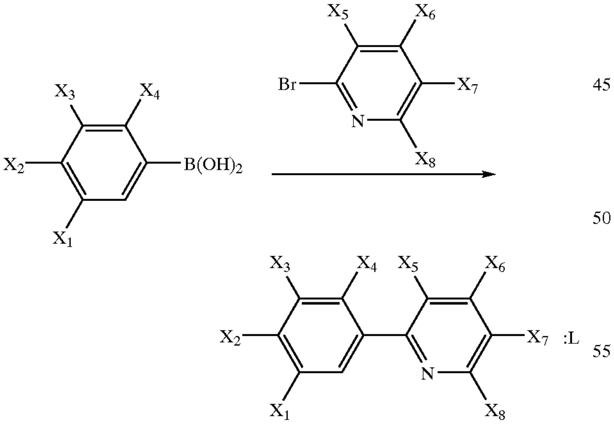

-continued

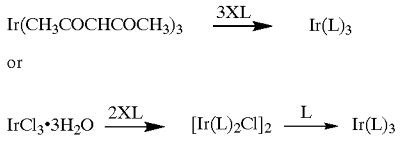

(Rhodium Complex)

Rh complex may be synthesized in the same manner as in Ir complex shown above.

(Palladium Complex)

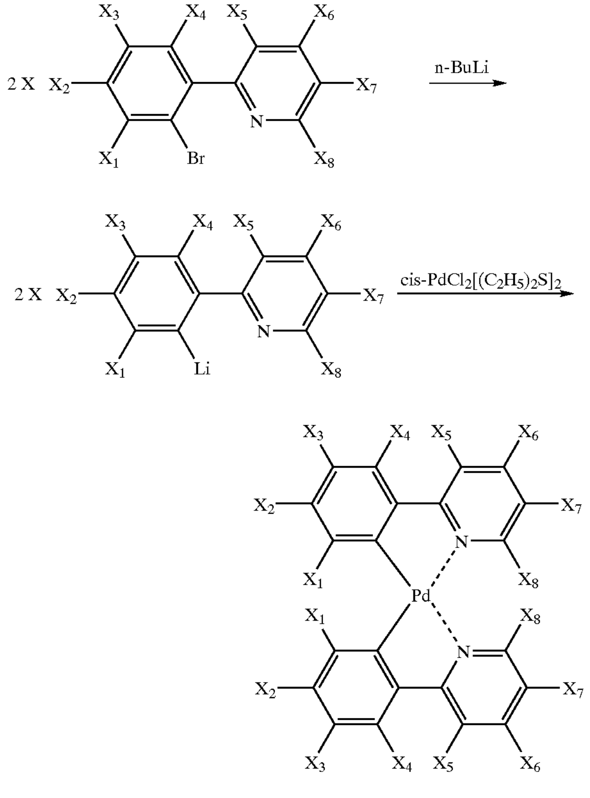

Bu: butyl

Specific and non-exhaustive examples of the metal coordination compound of formula (1) may include those (Example Compound Nos. (1—1) to (1-180)) shown in Tables 3–8 wherein Ex. Comp. Nos. (1—1) to (1-180) are simply indicated as (1) to (180), respectively.

TABLE 3

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (1) | Ir | 3 | H | H | F | H | H | H | H | H |
| (2) | Ir | 3 | H | F | H | H | H | H | H | H |
| (3) | Ir | 3 | H | H | Cl | H | H | H | H | H |

TABLE 3-continued

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (4) | Ir | 3 | H | H | F | H | H | $OCH_3$ | H | H |
| (5) | Ir | 3 | H | H | F | H | H | H | Br | H |
| (6) | Ir | 3 | H | $C_2H_5$ | H | H | H | H | H | H |
| (7) | Ir | 3 | H | H | $NO_2$ | H | H | H | H | H |
| (8) | Ir | 3 | H | H | $NO_2$ | H | H | H | $CF_3$ | H |
| (9) | Ir | 3 | H | H | $NO_2$ | H | H | $NO_2$ | H | H |
| (10) | Ir | 3 | H | H | $NO_2$ | H | H | $OC_{11}H_{23}$ | H | H |
| (11) | Ir | 3 | H | H | $C_3H_7$ | H | H | H | H | H |
| (12) | Ir | 3 | H | $C_2H_5$ | $OCH_3$ | H | H | H | H | H |
| (13) | Ir | 3 | H | H | $C_3H_7$ | H | H | $OC_4H_9$ | H | H |
| (14) | Ir | 3 | H | $C_{20}H_{41}$ | H | H | H | H | H | H |
| (15) | Ir | 3 | H | H | $OCH_3$ | H | H | H | H | H |
| (16) | Ir | 3 | H | $OCH_3$ | $OCH_3$ | H | H | H | H | H |
| (17) | Ir | 3 | H | H | $OCH(CH_3)_2$ | H | H | H | H | H |
| (18) | Ir | 3 | H | H | $OC_5H_{11}$ | H | H | H | H | H |
| (19) | Ir | 3 | H | H | $OC_{16}H_{33}$ | H | H | H | H | H |
| (20) | Ir | 3 | H | H | $OCH_3$ | H | H | $OCH_3$ | H | H |
| (21) | Ir | 3 | H | H | $OCH(CH_3)_2$ | H | H | $OCH_3$ | H | H |
| (22) | Ir | 3 | H | H | $OC_{10}H_{21}$ | H | H | $NO_2$ | H | H |
| (23) | Ir | 3 | H | H | $OCH(CH_3)_2$ | H | H | H | $CF_3$ | H |
| (24) | Ir | 3 | H | H | $SCH_3$ | H | H | H | H | H |
| (25) | Ir | 3 | H | $OCH_2CH{=}CH_2$ | H | H | H | H | H | H |
| (26) | Ir | 3 | H | H | $OCH_2C{\equiv}CCH_3$ | H | H | H | H | H |
| (27) | Ir | 3 | H | H | $COCH_3$ | H | H | H | H | H |
| (28) | Ir | 3 | H | H | $COCH_3$ | H | H | $NO_2$ | H | H |
| (29) | Ir | 3 | H | H | $COCH_3$ | H | H | H | $CF_3$ | H |
| (30) | Ir | 3 | H | H | $COCH_3$ | H | H | $OCH_3$ | H | H |

TABLE 4

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (31) | Ir | 3 | H | H | $COC_9H_{19}$ | H | H | H | H | H |
| (32) | Ir | 3 | H | H | $CF_3$ | H | H | H | H | H |
| (33) | Ir | 3 | H | H | $CF_3$ | H | H | H | $CF_3$ | H |
| (34) | Ir | 3 | H | H | $CF_3$ | H | H | $NO_2$ | H | H |
| (35) | Ir | 3 | H | H | $CF_3$ | H | H | $OCH(CH_3)_2$ | H | H |
| (36) | Ir | 3 | H | $C_3F_7$ | H | H | H | H | H | H |
| (37) | Ir | 3 | H | H | $OCF_3$ | H | H | H | H | H |
| (38) | Ir | 3 | H | $OCF_3$ | H | H | H | H | H | H |
| (39) | Ir | 3 | H | H | $OCF_3$ | H | H | $NO_2$ | H | H |
| (40) | Ir | 3 | H | H | $OCF_3$ | H | H | H | $CF_3$ | H |
| (41) | Ir | 3 | H | H | $OCF_3$ | H | H | $OCH_3$ | H | H |
| (42) | Ir | 3 | H | H | $OCH_2C_3F_7$ | H | H | H | H | H |
| (43) | Ir | 3 | H | $O(CH_2)_3C_2F_5$ | H | H | H | H | H | H |
| (44) | Ir | 3 | H | H | $O(CH_2)_3OCH_2C_2F_5$ | H | H | H | H | H |
| (45) | Ir | 3 | H | H | $COOC_2H_5$ | H | H | H | H | H |
| (46) | Ir | 3 | H | $OCOCH_3$ | H | H | H | H | H | H |
| (47) | Ir | 3 | H | H | $O(CH_2)_2C_3F_7$ | H | H | H | $C_5F_{11}$ | H |
| (48) | Ir | 3 | H | H | H | H | H | $OCH_3$ | H | H |
| (49) | Ir | 3 | H | H | H | H | H | H | $CF_3$ | H |
| (50) | Ir | 3 | H | H | H | H | H | H | $NO_2$ | H |
| (51) | Ir | 3 | H | H | $Si(CH_3)_3$ | H | H | H | H | H |
| (52) | Ir | 3 | H | H | $Si(CH_3)_2C_4H_9$ | H | H | H | H | H |
| (53) | Ir | 3 | H | $Si(CH_3)_2C_8H_{17}$ | H | H | H | H | H | H |
| (54) | Ir | 3 | H | H | $Si(C_2H_5)_3$ | H | H | H | H | H |
| (55) | Ir | 3 | H | H | H | H | H | $Si(CH_3)_2C_8H_{13}$ | H | H |
| (56) | Ir | 3 | H | $C_2H_5$ | $OCH_3$ | H | H | $OCH_3$ | H | H |
| (57) | Ir | 3 | H | F | H | F | H | $OCH_3$ | H | H |
| (58) | Ir | 3 | H | F | H | F | H | $OCH_3$ | $CF_3$ | H |
| (59) | Ir | 3 | H | H | $Si(CH_3)_3$ | H | H | H | Br | H |
| (60) | Ir | 3 | H | $Si(CH_3)_2C_7H_{15}$ | $OCH_3$ | H | H | H | H | H |

TABLE 5

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (61) | Rh | 3 | H | H | F | H | H | H | H | H |
| (62) | Rh | 3 | F | F | H | H | H | H | H | H |
| (63) | Rh | 3 | H | H | F | H | H | $OCH_3$ | H | H |
| (64) | Rh | 3 | H | H | $NO_2$ | H | H | H | H | H |
| (65) | Rh | 3 | H | H | $NO_2$ | H | H | $OC_8H_{17}$ | H | H |

TABLE 5-continued

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (66) | Rh | 3 | H | H | $C_2H_5$ | H | H | H | H | H |
| (67) | Rh | 3 | H | $C_2H_5$ | $OCH_3$ | H | H | H | H | H |
| (68) | Rh | 3 | H | $C_{12}H_{25}$ | H | H | H | H | H | H |
| (69) | Rh | 3 | H | $C_3H_7$ | H | H | H | $OCH_3$ | H | H |
| (70) | Rh | 3 | H | H | $OCH(CH_3)_2$ | H | H | H | H | H |
| (71) | Rh | 3 | H | H | $OC_{15}H_{31}$ | H | H | H | H | H |
| (72) | Rh | 3 | H | H | $OC_6H_{13}$ | H | H | $NO_2$ | H | H |
| (73) | Rh | 3 | H | H | $OCH_3$ | H | H | $OCH_3$ | H | H |
| (74) | Rh | 3 | H | H | $OCH(CH_3)_2$ | H | H | H | $CF_3$ | H |
| (75) | Rh | 3 | H | H | $OCH_2CH{=}CH_2$ | H | H | H | H | H |
| (76) | Rh | 3 | H | $OC{\equiv}CC_4H_9$ | H | H | H | H | H | H |
| (77) | Rh | 3 | H | H | $SC_2H_5$ | H | H | H | H | H |
| (78) | Rh | 3 | H | H | $SCH_3$ | H | H | $OCH_3$ | H | H |
| (79) | Rh | 3 | H | $SCH_3$ | $SCH_3$ | H | H | H | H | H |
| (80) | Rh | 3 | H | H | $COCH_3$ | H | H | H | H | H |
| (81) | Rh | 3 | H | H | $COCH_3$ | H | H | $OCH_3$ | H | H |
| (82) | Rh | 3 | H | H | $CF_3$ | H | H | H | H | H |
| (83) | Rh | 3 | H | H | $CF_3$ | H | H | $OCH(CH_3)_2$ | H | H |
| (84) | Rh | 3 | H | H | $OCF_3$ | H | H | H | $CF_3$ | H |
| (85) | Rh | 3 | H | H | $OCH_2C_4F_9$ | H | H | H | H | H |
| (86) | Rh | 3 | H | H | $O(CH_2)_6C_2F_5$ | H | H | H | H | H |
| (87) | Rh | 3 | H | H | H | H | H | $OCH_3$ | H | H |
| (88) | Rh | 3 | H | H | $Si(CH_3)_3$ | H | H | H | H | H |
| (89) | Rh | 3 | H | $Si(CH_3)_2C_6H_{13}$ | H | H | H | H | H | H |
| (90) | Rh | 3 | H | $Si(CH_3)_2C_7H_{15}$ | $OCH_3$ | H | H | H | H | H |

TABLE 6

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (91) | Pd | 2 | H | H | F | H | H | H | H | H |
| (92) | Pd | 2 | H | F | H | F | H | H | H | H |
| (93) | Pd | 2 | H | H | F | H | H | $OC_7H_{15}$ | H | H |
| (94) | Pd | 2 | H | H | $NO_2$ | H | H | H | H | H |
| (95) | Pd | 2 | H | H | $NO_2$ | H | H | $OC_5H_{11}$ | H | H |
| (96) | Pd | 2 | H | $C_2H_5$ | $OCH_3$ | H | H | H | H | H |
| (97) | Pd | 2 | H | H | $C_5H_{11}$ | H | H | $OCH_3$ | H | H |
| (98) | Pd | 2 | H | $C_{15}H_{31}$ | H | H | H | H | H | H |
| (99) | Pd | 2 | H | H | $OCH(CH_3)_2$ | H | H | H | H | H |
| (100) | Pd | 2 | H | H | $OC_3H_7$ | H | H | H | H | H |
| (101) | Pd | 2 | H | H | $COC_8H_{17}$ | H | H | H | H | H |
| (102) | Pd | 2 | H | H | $CF_3$ | H | H | H | H | H |
| (103) | Pd | 2 | H | H | $CF_3$ | H | H | $OCH(CH_3)_2$ | H | H |
| (104) | Pd | 2 | H | H | $OCF_3$ | H | H | H | $CF_3$ | H |
| (105) | Pd | 2 | H | H | $Si(CH_3)_3$ | H | H | H | H | H |
| (106) | Pd | 2 | H | H | F | H | H | $OC_5H_{11}$ | H | H |
| (107) | Pd | 2 | H | H | $NO_2$ | H | H | $OC_3H_7$ | H | H |
| (108) | Pd | 2 | H | H | $C_2H_5$ | H | H | $OCH_3$ | H | H |
| (109) | Pd | 2 | H | $C_{10}H_{21}$ | H | H | H | H | H | H |
| (110) | Pd | 2 | H | H | $COCH_3$ | H | H | H | H | H |
| (111) | Ir | 3 | H | Cl | $CF_3$ | H | H | H | H | H |
| (112) | Ir | 3 | H | Cl | $CF_3$ | H | H | H | CF3 | H |
| (113) | Ir | 3 | H | Cl | $CF_3$ | H | H | OCH3 | H | H |
| (114) | Rh | 3 | H | Cl | $CF_3$ | H | H | H | H | H |
| (115) | Rh | 3 | H | Cl | $CF_3$ | H | H | H | CF3 | H |
| (116) | Rh | 3 | H | Cl | $CF_3$ | H | H | CF3 | H | H |
| (117) | Rh | 3 | H | Cl | $CF_3$ | H | H | OCH3 | H | H |
| (118) | Rh | 3 | H | Cl | $CF_3$ | H | H | $C_2H_5$ | H | H |
| (119) | Pd | 2 | H | Cl | $CF_3$ | H | H | H | H | H |
| (120) | Pd | 2 | H | Cl | $CF_3$ | H | H | H | CF3 | CF3 |

TABLE 7

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (121) | Ir | 3 | H | F | $CF_3$ | H | H | H | H | H |
| (122) | Ir | 3 | H | F | H | F | H | H | H | H |
| (123) | Ir | 3 | H | $CF_3$ | H | $CF_3$ | H | H | H | H |
| (124) | Ir | 3 | H | $CF_3$ | H | F | H | H | H | H |
| (125) | Ir | 3 | H | $CF_3$ | $CF_3$ | H | H | H | Br | H |
| (126) | Ir | 3 | F | $C_2H_5$ | H | H | H | H | H | H |
| (127) | Ir | 3 | F | H | $NO_2$ | H | H | H | H | H |
| (128) | Ir | 3 | F | H | $NO_2$ | F | H | H | $CF_3$ | H |

TABLE 7-continued

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (129) | Ir | 3 | F | H | $NO_2$ | H | H | $NO_2$ | H | H |
| (130) | Ir | 3 | F | H | $NO_2$ | H | H | $OC_{11}H_{23}$ | H | H |
| (131) | Ir | 3 | F | H | $C_3H_7$ | H | H | H | H | H |
| (132) | Ir | 3 | F | $C_2H_5$ | $OCH_3$ | H | H | H | H | H |
| (133) | Ir | 4 | F | H | $C_3H_7$ | H | H | $OC_4H_9$ | H | H |
| (134) | Ir | 3 | H | $C_{20}H_{41}$ | H | F | H | H | H | H |
| (135) | Ir | 3 | H | H | $OCH_3$ | F | H | H | H | H |
| (136) | Ir | 3 | H | $OCH_3$ | $OCH_3$ | F | H | H | H | H |
| (137) | Ir | 3 | H | H | $OCH(CH_3)_2$ | F | H | H | H | H |
| (138) | Ir | 3 | H | H | $OC_5H_{11}$ | F | H | H | H | H |
| (139) | Ir | 3 | H | H | $OC_{16}H_{33}$ | F | H | H | H | H |
| (140) | Ir | 3 | H | H | $OCH_3$ | F | H | $OCH_3$ | H | H |
| (141) | Ir | 3 | H | H | $OCH(CH_3)_2$ | H | F | $OCH_3$ | H | H |
| (142) | Ir | 3 | H | H | $OC_{10}H_{21}$ | H | F | $NO_2$ | H | H |
| (143) | Ir | 3 | H | H | $OCH(CH_3)_2$ | H | F | H | $CF_3$ | H |
| (144) | Ir | 3 | H | H | $SCH_3$ | H | $C_2H_5$ | H | H | H |
| (145) | Ir | 3 | H | $OCH_2CH{=}CH_2$ | H | H | $C_2H_5$ | H | H | H |
| (146) | Ir | 3 | H | H | $OCH_2C{\equiv}CCH_3$ | H | H | H | H | F |
| (147) | Ir | 3 | H | H | $COCH_3$ | H | H | H | H | F |
| (148) | Ir | 3 | H | H | $COCH_3$ | H | H | $NO_2$ | H | F |
| (149) | Ir | 3 | H | H | $COCH_3$ | H | H | H | $CF_3$ | F |
| (150) | Ir | 3 | $CF_3$ | H | $COCH_3$ | H | H | $OCH_3$ | H | H |

TABLE 8

| No. | M | n | $X_1$ | $X_2$ | $X_3$ | $X_4$ | $X_5$ | $X_6$ | $X_7$ | $X_8$ |
|---|---|---|---|---|---|---|---|---|---|---|
| (151) | Ir | 3 | F | H | $COC_9H_{19}$ | H | H | H | H | H |
| (152) | Ir | 3 | H | $CF_3$ | H | F | H | H | H | H |
| (153) | Ir | 3 | F | H | $CF_3$ | H | H | H | $CF_3$ | H |
| (154) | Ir | 3 | H | H | $CF_3$ | F | H | $NO_2$ | H | H |
| (155) | Ir | 3 | H | H | $CF_3$ | F | H | $OCH(CH)_2$ | H | H |
| (156) | Ir | 3 | H | $C_3F_7$ | H | $CF_3$ | H | H | H | H |
| (157) | Ir | 3 | H | H | $OCF_3$ | H | $CF_3$ | H | H | H |
| (158) | Ir | 3 | H | $OCF_3$ | H | H | $C_2H_5$ | H | H | H |
| (159) | Ir | 3 | H | $CF_3$ | H | $CF_3$ | H | H | H | H |
| (160) | Ir | 3 | H | H | $OCF_3$ | H | F | H | $CF_3$ | H |
| (161) | Ir | 3 | H | H | $OCF_3$ | H | H | $OCH_3$ | H | F |
| (162) | Ir | 3 | H | H | $OCH_2C_3F_7$ | H | H | H | H | F |
| (163) | Ir | 3 | H | $O(CH_2)_3C_2F_5$ | H | H | H | H | H | F |
| (164) | Ir | 3 | H | H | $O(CH_2)_3OCH_2C_2F_5$ | Cl | H | H | H | H |
| (165) | Ir | 3 | H | H | $COOC_2H_5$ | F | H | H | H | H |
| (166) | Rh | 3 | H | $OCOCH_3$ | H | H | F | H | H | H |
| (167) | Rh | 3 | H | H | $O(CH_2)_2C_3F_7$ | H | $C_2H_5$ | H | $C_5F_{11}$ | H |
| (168) | Rh | 3 | H | H | H | H | H | $OCH_3$ | H | F |
| (169) | Rh | 3 | H | H | H | H | H | H | $CF_3$ | F |
| (170) | Rh | 3 | H | H | H | H | H | H | $NO_2$ | F |
| (171) | Rh | 3 | H | H | $Si(CH_3)_3$ | H | H | H | H | F |
| (172) | Rh | 3 | H | H | $Si(CH_3)_2C_4H_9$ | H | H | H | H | F |
| (173) | Rh | 3 | H | $Si(CH_3)C_8H_{17}$ | H | F | H | H | H | H |
| (174) | Rh | 3 | H | H | $Si(C_2H_5)_3$ | F | H | H | H | H |
| (175) | Rh | 3 | H | H | H | F | H | $Si(CH_3)C_6H_{13}$ | H | H |
| (176) | Pd | 2 | H | $C_2H_5$ | $OCH_3$ | F | H | $OCH_3$ | H | H |
| (177) | Pd | 2 | F | H | F | F | H | $OCH_3$ | H | H |
| (178) | Pd | 2 | F | H | F | F | H | $OCH_3$ | $CF_3$ | H |
| (179) | Pd | 2 | F | H | $Si(CH_3)_3$ | H | H | H | Br | H |
| (180) | Pd | 2 | F | $Si(CH_3)_2C_7H_{15}$ | $OCH_3$ | H | H | H | H | H |

The metal coordination compound of formula (2) may generally be synthesized through the following reaction scheme.

(Iridium Complex)

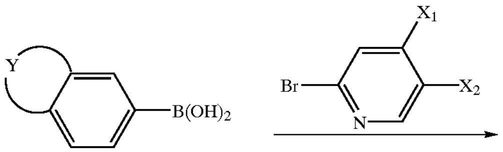

-continued

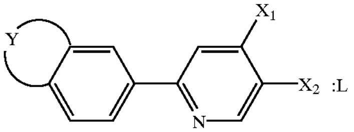

$Ir(CH_3COCHCOCH_3)_3$ 3XL $Ir(L)_3$ or $IrCl_3$ 2XL $[Ir(L)_2Cl]_2$ L $Ir(L)_3$ (Rhodium Complex)

Rh complex may be synthesized in the same manner as in Ir complex shown above.

(Palladium Complex)

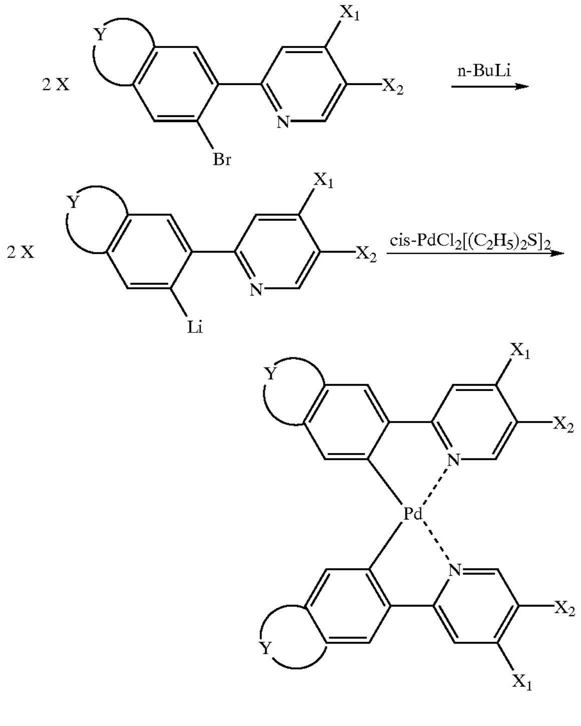

Bu: butyl

Specific and non-exhaustive examples of the metal coordination compound of formula (2) may include those (Example Compound Nos. (2-1) to (2-200) shown in Tables 9–15 wherein Ex. Comp. Nos. (2-1) to (2-200) are simply indicated as (1) to (200), respectively.

In Tables 9–15, symbols A to C' for alkylene group Y represents alkylene groups shown below.

A: $—CH_2CH_2—$

B: 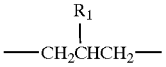

C: 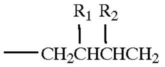

D: $—CH_2OCH_2—$

E: 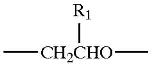

F: 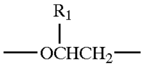

G: 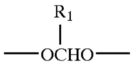

H: 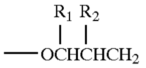

I: 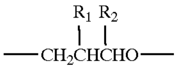

-continued

J: 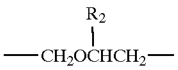

K: 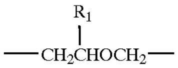

L: 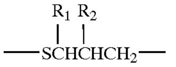

M: 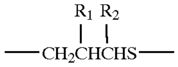

N: 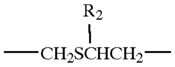

O: 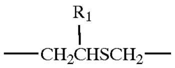

P: 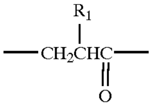

Q: 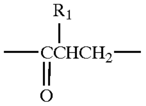

R: 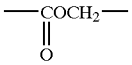

S: 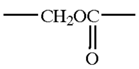

T: 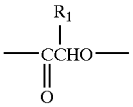

U: 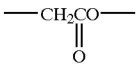

V: 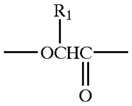

W: 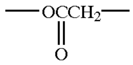

X: 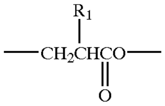

Z: 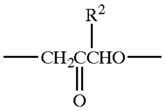

A': 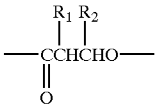

B': 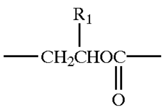

C': 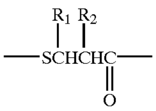

TABLE 9

| No | M | n | Y | $R_1$ | $R_2$ | $X_1$ | $X_2$ |
|---|---|---|---|---|---|---|---|
| (1) | Ir | 3 | A | — | — | H | H |
| (2) | Ir | 3 | A | — | — | $OCH_3$ | H |
| (3) | Ir | 3 | B | H | — | H | H |
| (4) | Ir | 3 | B | H | — | $OCH_3$ | H |
| (5) | Ir | 3 | B | H | — | H | $CF_3$ |
| (6) | Ir | 3 | B | H | — | H | Cl |
| (7) | Ir | 3 | B | $CH_3$ | — | H | H |
| (8) | Ir | 3 | B | $CH_3$ | — | F | H |
| (9) | Ir | 3 | B | $CH_3$ | — | $NO_2$ | H |
| (10) | Ir | 3 | B | $C_2H_5$ | — | H | H |
| (11) | Ir | 3 | B | $C_3H_7$ | — | H | $CF_3$ |
| (12) | Ir | 3 | B | $C_2H_5(CH_3)CHCH_2$ | — | H | H |
| (13) | Ir | 4 | B | $C_6H_{13}$ | — | $OCH(CH_3)_2$ | H |
| (14) | Ir | 3 | B | $C_{10}H_{21}$ | — | $Si(CH_3)_3$ | H |
| (15) | Ir | 3 | C | H | H | H | H |
| (16) | Ir | 3 | C | H | H | $OCH_3$ | H |
| (17) | Ir | 3 | C | H | H | H | $CF_3$ |
| (18) | Ir | 3 | C | H | H | F | H |
| (19) | Ir | 3 | C | H | H | $NO_2$ | H |
| (20) | Ir | 3 | C | H | H | $OC_5H_{11}$ | H |
| (21) | Ir | 3 | C | H | H | $O(CH_2)_2C_3F_7$ | H |
| (22) | Ir | 3 | C | H | H | H | $Si(C_2H_5)_3$ |
| (23) | Ir | 3 | C | H | H | H | Br |
| (24) | Ir | 3 | C | H | H | $CH_3$ | H |
| (25) | Ir | 3 | C | $CH_3$ | H | $CH_3$ | H |
| (26) | Ir | 3 | C | H | $CH_3$ | H | H |
| (27) | Ir | 3 | C | $CH_3$ | $CH_3$ | H | H |
| (28) | Ir | 3 | C | $C_3H_7$ | H | $Si(CH_3)_3$ | H |
| (29) | Ir | 3 | C | H | $C_5H_{11}$ | H | H |
| (30) | Ir | 3 | C | $C_8H_{17}$ | H | Cl | H |

TABLE 10

| No | M | n | Y | $R_1$ | $R_2$ | $X_1$ | $X_2$ |
|---|---|---|---|---|---|---|---|
| (31) | Ir | 3 | C | $C_2H_5$ | $C_2H_5$ | H | $C_7F_{15}$ |
| (32) | Ir | 3 | C | H | $C_6H_{13}$ | $NO_2$ | H |
| (33) | Ir | 3 | C | $C_{10}H_{21}$ | H | $CF_3$ | H |
| (34) | Ir | 3 | C | H | $C_9H_{19}$ | H | $OC_4H_9$ |
| (35) | Ir | 3 | D | — | — | H | H |
| (36) | Ir | 3 | D | — | — | $OCH_3$ | H |
| (37) | Ir | 3 | E | H | — | H | H |
| (38) | Ir | 3 | E | H | — | H | $NO_2$ |
| (39) | Ir | 3 | E | $CH_3$ | — | H | H |
| (40) | Ir | 3 | E | $CH_3$ | — | $OCH_3$ | H |
| (41) | Ir | 3 | E | $CH_3$ | — | H | $CF_3$ |
| (42) | Ir | 3 | E | $CH_3$ | — | $NO_2$ | H |
| (43) | Ir | 3 | E | $CH_3$ | — | $OC_3H_7$ | H |
| (44) | Ir | 3 | E | $C_2H_5$ | — | H | H |
| (45) | Ir | 3 | E | $C_2H_5$ | — | H | $CF_3$ |
| (46) | Ir | 3 | E | $C_3H_7$ | — | H | H |
| (47) | Ir | 3 | E | $C_3H_7$ | — | $OC_5H_{11}$ | H |
| (48) | Ir | 3 | E | $(CH_3)_2CHCH_2CH_2$ | — | H | H |
| (49) | Ir | 3 | E | $C_5H_{11}$ | — | H | $C_4F_9$ |
| (50) | Ir | 3 | E | $C_6H_{13}$ | — | H | H |
| (51) | Ir | 3 | E | $C_6H_{13}$ | — | H | Br |
| (52) | Ir | 3 | E | $C_6H_{13}$ | — | $NO_2$ | H |
| (53) | Ir | 3 | E | $C_8H_{17}$ | — | H | H |
| (54) | Ir | 3 | E | $C_9H_{19}$ | — | $OCH_2C{\equiv}CCH_3$ | H |
| (55) | Ir | 3 | E | $C_{10}H_{21}$ | — | H | H |
| (56) | Ir | 3 | E | $C_{10}H_{21}$ | — | $OCH_2CH{=}CH_2$ | H |
| (57) | Ir | 3 | F | H | — | $OCH_3$ | H |
| (58) | Ir | 3 | F | $CH_3$ | — | H | H |
| (59) | Ir | 3 | F | $CH_3$ | — | $OCH_3$ | H |
| (60) | Ir | 3 | F | $C_2H_5$ | — | H | $CF_3$ |

TABLE 11

| No | M | n | Y | $R_1$ | $R_2$ | $X_1$ | $X_2$ |
|---|---|---|---|---|---|---|---|
| (61) | Ir | 3 | F | $C_6H_{13}$ | — | $OCH(CH_3)_2$ | H |
| (62) | Ir | 3 | F | $C_8H_{17}$ | — | $Si(CH_3)_2C_8H_{17}$ | H |

TABLE 11-continued

| No | M | n | Y | $R_1$ | $R_2$ | $X_1$ | $X_2$ |
|---|---|---|---|---|---|---|---|
| (63) | Ir | 3 | G | H | — | $OCH_3$ | H |
| (64) | Ir | 3 | G | H | — | H | $CF_3$ |
| (65) | Ir | 3 | G | H | — | $O(CH_2)_3OCH_2C_2F_5$ | H |
| (66) | Ir | 3 | G | $CH_3$ | — | H | H |
| (67) | Ir | 3 | H | H | H | H | H |
| (68) | Ir | 3 | H | $CH_3$ | H | $Si(CH_3)_3$ | H |
| (69) | Ir | 3 | H | H | $CH_3$ | H | Cl |
| (70) | Ir | 3 | I | H | H | H | H |
| (71) | Ir | 3 | I | H | H | $OCH_3$ | H |
| (72) | Ir | 3 | I | H | H | H | $CF_3$ |
| (73) | Ir | 3 | I | H | H | H | $CH_3$ |
| (74) | Ir | 3 | I | $C_2H_5$ | H | $COOC_2H_5$ | H |
| (75) | Ir | 3 | I | H | $C_5H_{11}$ | $OCH_2CH{=}CH_2$ | H |
| (76) | Ir | 3 | J | H | — | H | H |
| (77) | Ir | 3 | J | H | — | $NO_2$ | H |
| (78) | Ir | 3 | J | $CH_3$ | — | $OCH_3$ | H |
| (79) | Ir | 3 | K | H | — | H | H |
| (80) | Ir | 3 | K | H | — | H | $Si(CH_3)_3$ |
| (81) | Ir | 3 | K | $C_3H_7$ | — | H | $CF_3$ |
| (82) | Ir | 3 | L | H | H | H | H |
| (83) | Ir | 3 | L | $CH_3$ | H | $SC_2H_5$ | H |
| (84) | Ir | 3 | L | H | $CH_3$ | $OC_6H_{13}$ | H |
| (85) | Ir | 3 | M | H | H | H | H |
| (86) | Ir | 3 | M | $C_2H_5$ | H | $COOC_3H_7$ | H |
| (87) | Ir | 3 | M | H | $C_2H_5$ | H | $O(CH_2)_3C_2F_5$ |
| (88) | Ir | 3 | N | — | H | H | H |
| (89) | Ir | 3 | N | — | $C_2H_5$ | H | $NO_2$ |
| (90) | Ir | 3 | N | — | $C_6H_{13}$ | Cl | H |

TABLE 12

| No | M | n | Y | $R_1$ | $R_2$ | $X_1$ | $X_2$ |
|---|---|---|---|---|---|---|---|
| (91) | Ir | 3 | O | H | — | H | H |
| (92) | Ir | 3 | O | H | — | H | $Si(C_2H_5)_3$ |
| (93) | Ir | 3 | O | $C_8H_{17}$ | — | $OCH(CH_3)_2$ | H |
| (94) | Ir | 3 | P | H | — | H | H |
| (95) | Ir | 3 | P | $C_3H_7$ | — | H | $COOCH_3$ |
| (96) | Ir | 3 | P | $C_6H_{13}$ | — | H | H |
| (97) | Ir | 3 | Q | H | — | H | H |
| (98) | Ir | 3 | Q | $C_4H_9$ | — | $O(CH_2)_3CH{=}CH_2$ | H |
| (99) | Ir | 3 | R | — | — | H | H |
| (100) | Ir | 3 | R | — | — | H | $CF_3$ |
| (101) | Ir | 3 | S | — | — | H | H |
| (102) | Ir | 3 | S | — | — | $OC_2H_5$ | H |
| (103) | Ir | 3 | T | H | — | H | Br |
| (104) | Ir | 3 | T | $C_2H_5$ | — | H | H |
| (105) | Ir | 3 | U | — | — | H | H |
| (106) | Ir | 3 | U | — | — | H | $C_7F_{15}$ |
| (107) | Ir | 3 | V | H | — | H | H |
| (108) | Ir | 3 | W | — | — | $OCH_2C{\equiv}CCH_3$ | H |
| (109) | Ir | 3 | X | $CH_3$ | — | H | H |
| (110) | Ir | 3 | Z | — | H | $O(CH_2)_2CH(CH_3)_2$ | H |
| (111) | Ir | 3 | Z | — | $C_3H_7$ | H | H |
| (112) | Ir | 3 | A' | H | H | H | H |
| (113) | Ir | 3 | B' | H | — | H | $NO_2$ |
| (114) | Ir | 3 | B' | $CH_3$ | — | H | H |
| (115) | Ir | 3 | C' | H | $C_9H_{19}$ | $OCH_3$ | H |
| (116) | Pt | 2 | A | — | — | H | H |
| (117) | Pt | 2 | B | H | — | H | H |
| (118) | Pt | 2 | B | H | — | H | $C_4F_9$ |
| (119) | Pt | 2 | B | $CH_3$ | — | $OCH_3$ | H |
| (120) | Pt | 2 | B | $C_3H_7$ | — | H | $CF_3$ |

TABLE 13

| No | M | n | Y | $R_1$ | $R_2$ | $X_1$ | $X_2$ |
|---|---|---|---|---|---|---|---|
| (121) | Pt | 2 | B | $C_8H_{17}$ | — | H | H |
| (122) | Pt | 2 | C | H | H | H | H |
| (123) | Pt | 2 | C | H | H | H | $CF_3$ |

TABLE 13-continued

| No | M | n | Y | $R_1$ | $R_2$ | $X_1$ | $X_2$ |
|---|---|---|---|---|---|---|---|
| (124) | Pt | 2 | C | $CH_3$ | $CH_3$ | H | H |
| (125) | Pt | 2 | C | $C_2H_5$ | H | H | H |
| (126) | Pt | 2 | C | $C_{10}H_{21}$ | H | $OCH_3$ | H |
| (127) | Pt | 2 | D | — | — | H | H |
| (128) | Pt | 2 | E | H | — | H | H |
| (129) | Pt | 2 | E | $CH_3$ | — | H | H |
| (130) | Pt | 2 | E | $CH_3$ | — | H | H |
| (131) | Pt | 2 | E | $CH_3$ | — | H | $NO_2$ |
| (132) | Pt | 2 | E | $C_6H_{13}$ | — | $OC_2H_5$ | H |
| (133) | Pt | 2 | F | $CH_3$ | — | H | H |
| (134) | Pt | 2 | F | $C_2H_5$ | — | H | $CF_3$ |
| (135) | Pt | 2 | G | H | — | H | H |
| (136) | Pt | 2 | G | H | — | H | $Si(CH_3)_3$ |
| (137) | Pt | 2 | G | $C_4H_9$ | — | H | $CH_3$ |
| (138) | Pt | 2 | H | H | $C_6H_{13}$ | H | H |
| (139) | Pt | 2 | I | H | H | H | H |
| (140) | Pt | 2 | I | $C_2H_5$ | H | H | $Si(C_2H_5)_3$ |
| (141) | Pt | 2 | J | — | H | H | H |
| (142) | Pt | 2 | K | $C_5H_{11}$ | — | H | H |
| (143) | Pt | 2 | L | $C_7H_{17}$ | H | $SC_2H_5$ | H |
| (144) | Pt | 2 | N | — | H | H | H |
| (145) | Pt | 2 | O | H | — | H | H |
| (146) | Pt | 2 | P | H | — | H | H |
| (147) | Pt | 2 | Q | H | — | H | $CH_3$ |
| (148) | Pt | 2 | R | — | — | H | H |
| (149) | Pt | 2 | U | — | — | H | H |
| (150) | Pt | 2 | V | H | — | $NO_2$ | H |

TABLE 14

| No | M | n | Y | $R_1$ | $R_2$ | $X_1$ | $X_2$ |
|---|---|---|---|---|---|---|---|
| (151) | Pt | 2 | W | — | — | H | H |
| (152) | Pt | 2 | X | $CH_3$ | — | H | H |
| (153) | Pt | 2 | Z | — | H | H | H |
| (154) | Pt | 2 | A' | H | H | H | H |
| (155) | Pt | 2 | B' | H | — | $OCH_3$ | H |
| (156) | Pt | 2 | C' | H | H | H | $CF_3$ |

TABLE 14-continued

| No | M | n | Y | $R_1$ | $R_2$ | $X_1$ | $X_2$ |
|---|---|---|---|---|---|---|---|
| (157) | Rh | 3 | B | H | — | H | Br |
| (158) | Rh | 3 | B | H | — | $OC_6H_{13}$ | H |
| (159) | Rh | 3 | B | $CH_3$ | — | H | H |
| (160) | Rh | 3 | C | H | H | H | H |
| (161) | Rh | 3 | C | H | H | $OCH_3$ | H |
| (162) | Rh | 3 | C | H | H | $NO_2$ | H |
| (163) | Rh | 3 | C | H | $CH_3$ | H | H |
| (164) | Rh | 3 | C | $C_6H_{13}$ | H | H | $Si(CH_3)_3$ |
| (165) | Rh | 3 | D | — | — | H | H |
| (166) | Rh | 3 | E | H | — | $COOC_2H_5$ | H |
| (167) | Rh | 3 | E | $CH_3$ | — | H | H |
| (168) | Rh | 3 | E | $CH_3$ | — | H | $O(CH_2)_6C_2F_5$ |
| (169) | Rh | 3 | E | $C_3H_7$ | — | H | H |
| (170) | Rh | 3 | E | $C_{10}H_{21}$ | — | H | H |
| (171) | Rh | 3 | F | $C_8H_{17}$ | — | H | H |
| (172) | Rh | 3 | G | H | — | $OCH_2CH{=}CH_2$ | H |
| (173) | Rh | 3 | G | $CH_3$ | — | H | $CF_3$ |
| (174) | Rh | 3 | H | H | H | H | H |
| (175) | Rh | 3 | I | H | H | H | H |
| (176) | Rh | 3 | K | $C_2H_5$ | — | Cl | H |
| (177) | Rh | 3 | M | H | H | H | H |
| (178) | Rh | 3 | N | — | H | H | H |
| (179) | Rh | 3 | P | $CH_3$ | — | H | $NO_2$ |
| (180) | Rh | 3 | S | — | — | H | H |

TABLE 15

| No | M | n | Y | $R_1$ | $R_2$ | $X_1$ | $X_2$ |
|---|---|---|---|---|---|---|---|
| (181) | Rh | 3 | V | H | — | H | H |
| (182) | Rh | 3 | X | H | — | $SC_5H_{11}$ | H |
| (183) | Rh | 3 | C' | H |  | $OC_7H_{15}$ | H |
| (184) | Pd | 2 | B | $C_6H_{13}$ | — | H | H |
| (185) | Pd | 2 | C | H | H | $OCH_3$ | H |
| (186) | Pd | 2 | C | H | H | H | H |
| (187) | Pd | 2 | D | — | — | H | H |
| (188) | Pd | 2 | E | H | — | H | $CF_3$ |
| (189) | Pd | 2 | E | $CH_3$ | — | H | H |
| (190) | Pd | 2 | F | $C_3H_7$ | — | H | H |
| (191) | Pd | 2 | G | H | — | H | H |
| (192) | Pd | 2 | G | H | — | $Si(CH_3)_3$ | H |
| (193) | Pd | 2 | I | $CH_3$ | H | $NO_2$ | H |
| (194) | Pd | 2 | J | — | H | H | H |
| (195) | Pd | 2 | L | H | H | H | H |
| (196) | Pd | 2 | M | H | H | $C_4F_9$ | H |
| (197) | Pd | 2 | O | H | — | H | $C_4H_9$ |
| (198) | Pd | 2 | T | H | — | H | H |
| (199) | Pd | 2 | W | — | — | $OCH_3$ | $OCH_3$ |
| (200) | Pd | 2 | A' | $CH_3$ | H | H | Cl |

Hereinbelow, the present invention will be described more specifically based on Examples with reference to the drawing.

EXAMPLES I-1–I-10

In these examples, metal coordination compounds of formula (1) (Ex. Comp. Nos. (I-4), (I-7), (I-17), (I-18), (I-21), (I-23), (I-32), (I-56), (I-67) and (I-74) were used in respective luminescence layers for Examples I-1–I-10, respectively.

Each of luminescence devices having a structure shown in FIG. 1B were prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 $mm^2$.

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (20 nm): mixture of CBP: metal coordination compound of formula (1) (95:5 by weight)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

Each of the thus-prepared luminescence devices was taken out of the vacuum chamber and was subjected to a continuous energization test in an atmosphere of dry nitrogen gas stream so as to remove device deterioration factors, such as oxygen and moisture (water content).

The continuous energization test was performed by continuously applying a voltage at a constant current density of 70 $mA/cm^2$ to the luminescence device having the ITO (transparent) electrode (as an anode) and the Al (metal) electrode (as a cathode), followed by measurement of luminance (brightness) with time so as to determine a time (luminance half-life) required for decreasing an initial luminance (70–120 $cd/m^2$) to ½ thereof.

The results are shown in Table 16 appearing hereinafter.

COMPARATIVE EXAMPLE I-1

A comparative luminescence device was prepared and evaluated in the same manner as in Example I-1–I-10 except that the metal coordination compound of formula (1) was changed to Ir-phenylpyridine complex ($Ir(ppy)_3$) shown below.

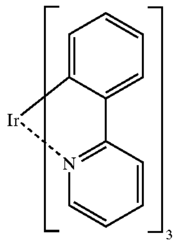

The results are shown in Table 16 below.

TABLE 16

| Ex. No. | Ex. Comp. No. | Luminance half-life (Hr) |
|---|---|---|
| I-1 | (I-4) | 750 |
| I-2 | (I-7) | 500 |
| I-3 | (I-17) | 900 |
| I-4 | (I-18) | 850 |
| I-5 | (I-21) | 850 |
| I-6 | (I-23) | 500 |
| I-7 | (I-32) | 600 |
| I-8 | (I-56) | 700 |
| I-9 | (I-67) | 400 |
| I-10 | (I-74) | 450 |
| Comp Ex. I-1 | $Ir(ppy)_3$ | 350 |

As is apparent from Table 16, compared with the conventional luminescence device using $Ir(ppy)_3$, the luminescence devices using the metal coordination compounds of formula (1) according to the present invention provide longer luminance half-lifes, thus resulting in an EL device having a high durability (luminance stability) based on a good stability of the metal coordination compound of formula (1) of the present invention.

EXAMPLES I-11–I-13

In these examples, metal coordination compounds of formula (1) (Ex. Comp. Nos. (I-1), (I-32) and (I-49) were used in respective luminescence layers for Examples I-11–I-13, respectively.

Each of luminescence devices having a structure shown in FIG. 1C were prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 $mm^2$.

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (20 nm): mixture of CBP: metal coordination compound of formula (1) (93:7 by weight)

Organic layer 3 (exciton diffusion prevention layer 17) (10 nm): BCP

Organic layer 4 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

Separately, each of the metal coordination compounds of formula (1) (Ex. Comp. Nos. (I-1), (I-32) and (I-49)) for the thus-prepared luminescence devices was subjected to measurement of photoluminescence spectrum in order to evaluate a luminescent characteristic of the metal coordination compounds of formula (1) (Ex. Comp. Nos. (I-1), (I-32) and (I-49)). Specifically, each of the metal coordination compounds was dissolved in toluene at a concentration of $10^{-4}$ mol/l and subjected to measurement of photo-luminescence spectrum at 25° C. by using excited light (ca. 350 nm) and a spectrophoto-fluorometer ("Model F4500", mfd. by Hitachi K.K.).

The results are shown in Table 17 appearing hereinafter.

The values of photoluminescence spectrum of the metal coordination compounds (Ex. Comp. Nos. (I-1), (I-32) and (I-49)) were substantially equivalent to those in the luminescence devices under voltage application as shown in Table 17, whereby it was confirmed that luminescence caused by the luminescence device was based on luminescence of the metal coordination compound used.

EL characteristics of the luminescence devices using the metal coordination compounds of formula (1) (Ex. Comp. Nos. (I-1), (I-32) and (I-49)) were measured by using a microammeter ("Model 4140B", mfd. by Hewlett-Packard Co.) for a current density under application of a voltage of 12 volts (current-voltage characteristic), using a spectrophotofluoro-meter ("Model SR1", mfd. by Topcon K.K.) for a peak emission wavelength $\lambda_{PE}$ (luminescence spectrum), and using a luminance meter ("Model BM7", mfd. by Topcon K.K.) for a luminescence efficiency (luminescence luminance). Further, an energy conversion efficiency was obtained according to the following equation:

Energy conversion efficiency (lm/W)=(π×luminescence efficiency (cd/A))/applied voltage (V).

All the above-prepared luminescence devices showed a good rectification characteristic.

The results are shown in Table 17.

COMPARATIVE EXAMPLE I-2

A comparative luminescence device was prepared and evaluated in the same manner as in Example I-2–I-13 except that the metal coordination compound of formula (1) was changed to Ir-phenylpyridine complex ($Ir(ppy)_3$) shown below.

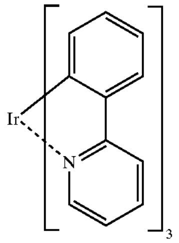

The results are shown in Table 17 below.

TABLE 17

| Ex. No | Ex. Comp. No. | λPE in toluene (nm) | λPE (nm) | Energy conversion efficiency (lm/W) | Luminescence efficiency (cd/A) | Current density ($mA/cm^2$ at 12 V) | Luminance half-life (Hr) |
|---|---|---|---|---|---|---|---|
| I-11 | (I-1) | 522 | 525 | 4.0 | 13.6 | 170 | 300 |
| I-12 | (I-32) | 487 | 525 | 0.4 | 2.4 | 130 | 400 |
| I-13 | (I-49) | 537 | 545 | 2.1 | 7.0 | 25 | 250 |
| Comp. Ex. I-2 | $Ir(ppy)_3$ | 510 | 510 | 6.0 | 19.0 | 20 | 150 |

As shown in Table 17, compared with the luminescence device using $Ir(ppy)_3$ (Comparative Example I-2) showing $\lambda_{PE}$=510 nm, the luminescence devices using the metal coordination compound of formula (1) according to the present invention showed longer peak emission wavelengths ($\lambda_{PE}$=525–545 nm) by 15–35 nm, thus resulting in smaller relative luminous efficiencies.

Smaller energy conversion efficiencies (0.4–4.0 lm/W) and luminescence efficiencies (2.4–13.6 cd/A) of the luminescence devices of the present invention compared with those (6.0 lm/W and 19.0 cd/A) of the luminescence device using $Ir(ppy)_3$ may be attributable to the smaller relative luminous efficiencies due to the longer peak emission wavelengths, thus not resulting in essentially inferior luminescent characteristics of the luminescence devices using the metal coordination compound of formula (1) of the present invention.

As apparent from the results of the luminance half-lifes of the luminescence devices, compared with the luminescence device using $Ir(ppy)_3$ showing the luminance half-life of 150 hours, the luminescence devices using the metal coordination compounds of formula (1) according to the present invention showed considerably longer luminance half-lifes of 250–400 hours.

EXAMPLE I-14

(Synthesis of Ex. Comp. No. (I-1))

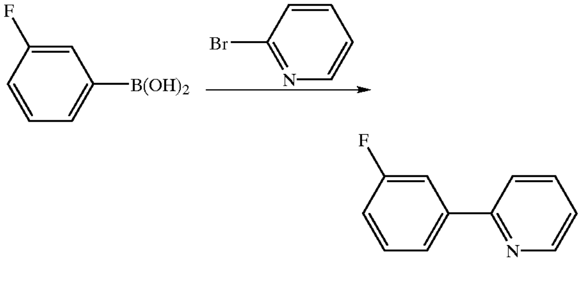

In a 1 liter-three necked flask, 20.0 g (126.6 mM) of 2-bromopyridine, 17.7 g (126.4 mM) of 3-fluorophenylbronic acid, 130 ml of toluene, 65 ml of ethanol and 130 ml of 2M-sodium carbonate aqueous solution were placed and stirred in a nitrogen gas stream at room temperature. Under stirring, to the mixture, 4.60 g (3.98 mM) of tetrakis (triphenyl-phosphine) palladium (0) was added, followed by heat-refluxing for 6 hours under stirring in nitrogen gas stream.

After the reaction, the reaction mixture was cooled, followed by extraction with cool water and toluene. The organic layer was washed with water until the system showed neutral, followed by distilling off of the solvent under reduced pressure to obtain a residue. The residue was purified by silica gel column chromatography (eluent: toluene/ethyl acetate=5/1) to obtain 6.0 g of 2-(3-fluorophenyl)pyridine (pale brown liquid) (Yield: 34.6%).

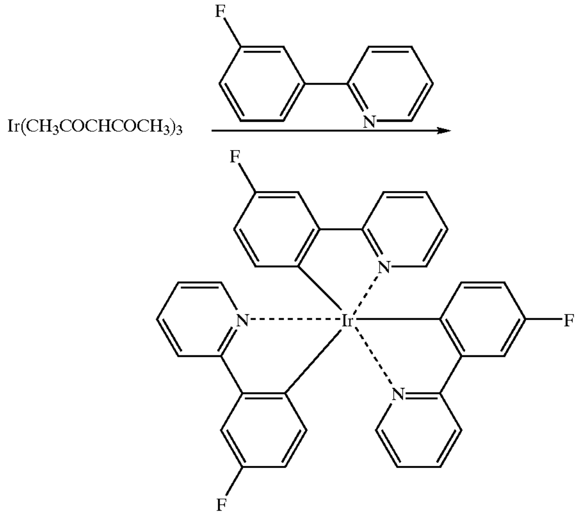

In a 100 ml-four necked flask, 50 ml of glycerol was placed and heat-stirred for 2 hours at 130–140√ C. while supplying nitrogen gas therein in the form of bubbles, followed by cooing to 100° C. by standing. To glycerol, 1.04 g (6.00 mM) of 2-(3-fluorophenyl)pyridine and 0.50 g (1.02 mM) of Iridium (III) acetylacetonate were added, followed by heat-refluxing for 10 hours under stirring in nitrogen gas stream.

After the reaction, the reaction mixture was cooled to room temperature and poured into 300 ml of 1N-HCl. The resultant precipitate was recovered by filtration and washed with water, followed by drying for 5 hours at 100° C. under reduced pressure and purification by silica gel column chromatography (eluent: chloroform) to obtain 0.22 g of Iridium (III) tris[2-(3-fluorophenyl)pyridine] (yellow powder) (Yield: 31.0%).

EXAMPLE I-15

(Synthesis of Ex. Comp. No. (I-32))

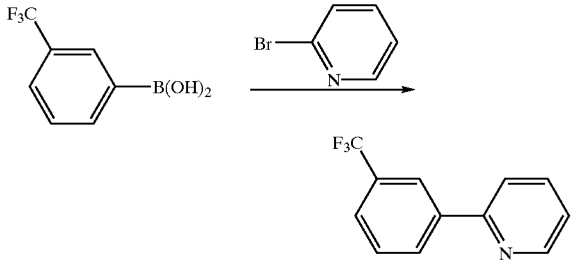

In a 1 liter-three necked flask, 20.8 g (131.6 mM) of 2-bromopyridine, 25.0 g (131.6 mM) of 3-trifluoromethylphenylbronic acid, 130 ml of toluene, 65 ml of ethanol and 130 ml of 2M-sodium carbonate aqueous solution were placed and stirred in a nitrogen gas stream at room temperature. Under stirring, to the mixture, 4.76 g (4.12 mM) of tetrakis (triphenyl-phosphine) palladium (0) was added, followed by heat-refluxing for 7 hours under stirring in nitrogen gas stream.

After the reaction, the reaction mixture was cooled, followed by extraction with cool water and toluene. The organic layer was washed with water until the system showed neutral, followed by distilling off of the solvent under reduced pressure to obtain a residue (pale brown liquid). The residue was purified by silica gel column chromatography (eluent: toluene/hexane=1/1) to obtain 6.0 g of 2-(3-trifluoromethylphenyl)pyridine (pale brown liquid) (Yield: 21.1%).

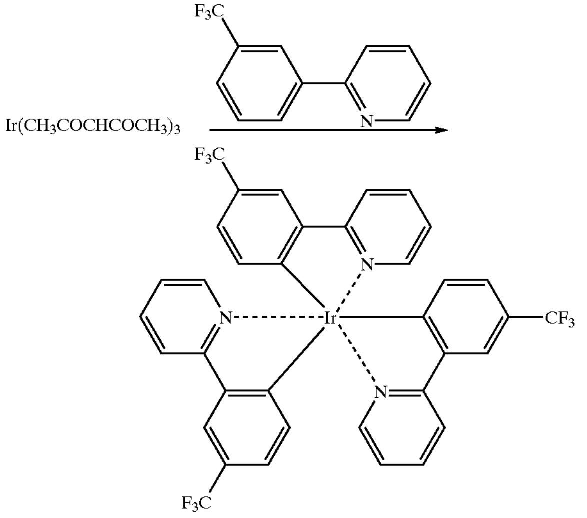

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 2.68 g (12.0 mM) of 2-(3-trifluoromethylphenyl)pyridine and 1.00 g (2.04 mM) of Iridium (III) acetylacetonate were added, followed by heat-refluxing for 10 hours under stirring in nitrogen gas stream.

After the reaction, the reaction mixture was cooled to room temperature and poured into 600 ml of 1N-HCl. The resultant precipitate was recovered by filtration and washed with water, followed by drying for 5 hours at 100°°C. under reduced pressure. The precipitate was dissolved in chloroform and the insoluble matter was removed by filtration, followed by purification by silica gel column chromatography (eluent: chloroform) and recyrstallization from a mixture solvent (chloroform/methanol) to obtain 0.62 g of Iridium (III) tris[2-(3-trifluoromethylphenyl)-pyridine] (yellow powder) (Yield: 35.3%), which showed a peak emission wavelength $\lambda_{PE}$ in toluene at 25° C. of 487 nm.

EXAMPLE I-16

(Synthesis of Ex. Comp. No. (I-49))

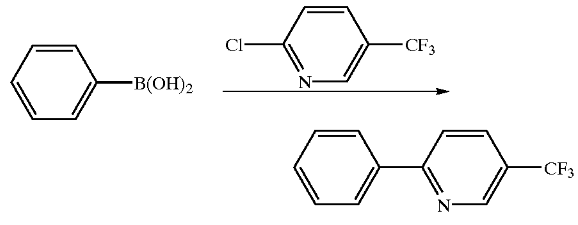

In a 1 liter-three necked flask, 25.6 g (141.0 mM) of 2-chloro-5-trifluoromethylpyridine, 17.2 g (141.0 mM) of phenylbronic acid, 140 ml of toluene, 70 ml of ethanol and 140 ml of 2M-sodium carbonate aqueous solution were placed and stirred in a nitrogen gas stream at room temperature. Under stirring, to the mixture, 5.10 g (4.41 mM) of tetrakis (triphenyl-phosphine) palladium (0) was added, followed by heat-refluxing for 6 hours under stirring in nitrogen gas stream.

After the reaction, the reaction mixture was cooled, followed by extraction with cool water and toluene. The organic layer was washed with water until the system showed neutral, followed by distilling off of the solvent under reduced pressure to obtain a residue. The residue was purified by silica gel column chromatography (eluent: toluene/hexane=5/1). The resultant creamy crystal was purified by alumina column chromatography (eluent: toluene) and recrystallized from ethanol to obtain 13.1 g of 2-phenyl-5-trifluoromethylpyridine (colorless crystal) (Yield: 41.6%).

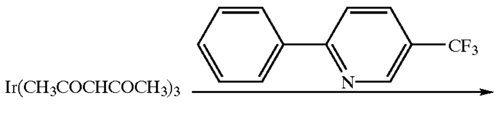

-continued

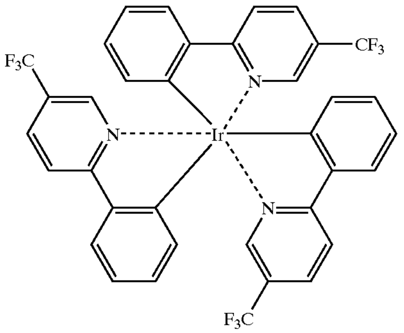

In a 200 ml-four necked flask, 100 ml of glycerol was placed and heat-stirred for 2 hours at 130–140° C. while supplying nitrogen gas therein in the form of bubbles, followed by cooing to 100° C. by standing. To glycerol, 2.68 g (12.0 mM) of 2-phenyl-5-trifluoromethylpyridine and 1.00 g (2.04 mM) of Iridium (III) acetylacetonate were added, followed by heat-refluxing for 8 hours under stirring in nitrogen gas stream.

After the reaction, the reaction mixture was cooled to room temperature and poured into 600 ml of 1N-HCl. The resultant precipitate was recovered by filtration and washed with water, followed by drying for 4 hours at 100° C. under reduced pressure and purification by silica gel column chromatography (eluent: chloroform) to obtain 0.43 g of Iridium (III) tris-(2-phenyl-5-trifluoromethylpyridine) (orange powder) (Yield: 24.5%).

EXAMPLE I-17

(Synthesis of Ex. Comp. No. (I-122))

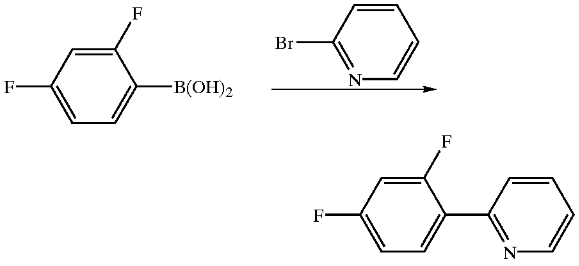

In a 100 ml-three necked flask, 3.16 g (19.9 mM) of 2-bromopyridine, 3.16 g (20.0 mM) of 2,4-difluorophenylbronic acid, 15 ml of toluene, 7.5 ml of ethanol and 15 ml of 2M-sodium carbonate aqueous solution were placed and stirred in a nitrogen gas stream at room temperature. Under stirring, to the mixture, 0.72 g (0.62 mM) of tetrakis (triphenyl-phosphine) palladium (0) was added, followed by heat-refluxing for 8 hours and 40 minutes under stirring in nitrogen gas stream.

After the reaction, the reaction mixture was cooled, followed by extraction with cool water and ethyl acetate. The organic layer was washed with water followed by distilling off of the solvent under reduced pressure to obtain a residue. The residue was purified by silica gel column chromatography (eluent: toluene/ethyl acetate=10/1) to obtain 3.28 g of 2-(2,4-difluorophenyl)pyridine (pale yellow oily product) (Yield: 86.0%).

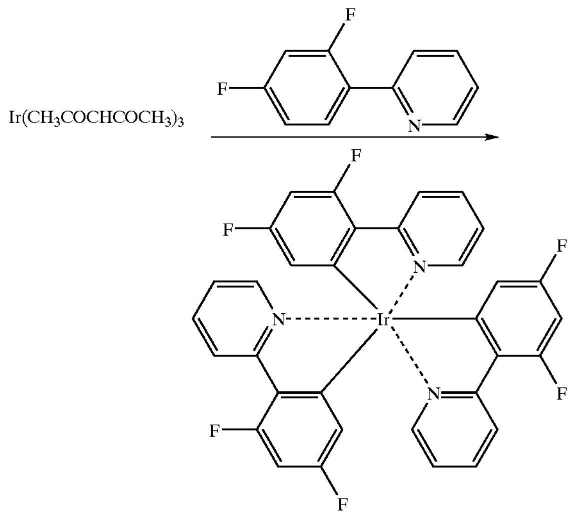

In a 100 ml-four necked flask, 50 ml of glycerol was placed and heat-stirred for 2 hours at 130–140° C. while supplying nitrogen gas therein in the form of bubbles, followed by cooing to 100° C. by standing. To glycerol, 0.96 g (5.02 mM) of 2-(2,4-difluorophenyl)pyridine and 0.50 g (1.02 mM) of Iridium (III) acetylacetonate were added, followed by heat-refluxing for 10 hours under stirring in nitrogen gas stream.

After the reaction, the reaction mixture was cooled to room temperature and poured into 300 ml of 1N-HCl. The resultant precipitate was recovered by filtration and washed with water, followed by drying for 5 hours at 100° C. under reduced pressure and purification by silica gel column chromatography (eluent: chloroform) and recrystallization from a mixture solvent (chloroform/methanol) to obtain 0.25 g of Iridium (III) tris[2-(4,6-difluorophenyl)-pyridine] (yellow powder) (Yield: 32.1%), which showed a peak emission wavelength $\lambda_{PE}$ in toluene at 25° C. of 471 nm.

EXAMPLE I-18

(Synthesis of Ex. Comp. No. (I-121))

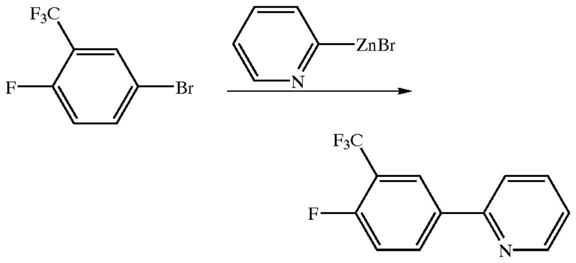

In a 500 ml-three necked flask, 11.0 g (45.3 mM) of 5-bromo-2-fluorobenzotrifluoride and 90 ml of dry tetrahydrofuran (THF) were placed and stirred in a nitrogen gas stream at room temperature. Under stirring, to the mixture, 2.60 g (2.25 mM) of tetrakis(triphenylphosphine) palladium (0) was added, followed by cooling to 20–21° C. (inner temperature) on an ice bath in nitrogen gas stream. At that temperature, 90 ml of 0.5 M-THF solution of 2-pyridylzinc bromide was gradually added dropwise to the mixture in nitrogen gas stream, followed by stirring for 4 hours at that temperature.

After the reaction, the reaction mixture was poured into cool water, followed by addition of ethyl acetate to remove the insoluble matter by filtration. The organic layer was washed with water and dried with anhydrous sodium sulfate, followed by distilling-off of the solvent under reduced pressure to obtain a residue.

The residue was purified by silica gel column chromatography (eluent: hexane/ethyl acetate=20/1) to obtain 1.80 g of 2-(4-fluoro-3-trifluoromethyl-phenyl)pyridine (pale brown oily product) (Yield: 16.6%)

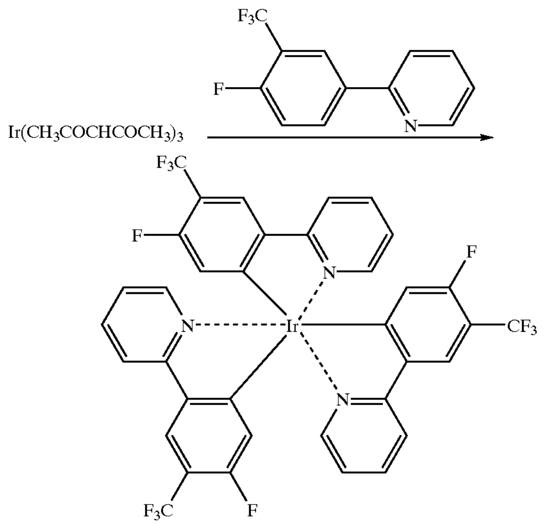

In a 100 ml-four necked flask, 50 ml of glycerol was placed and heat-stirred for 2 hours at 130–140° C. while supplying nitrogen gas therein in the form of bubbles, followed by cooing to 100°°C. by standing. To glycerol, 1.21 g (5.02 mM) of 2-(4-fluoro-3-trifluoromethylphenyl) pyridine and 0.50 g (1.02 mM) of Iridium (III) acetylacetonate were added, followed by heat-refluxing for 10 hours under stirring in nitrogen gas stream.

After the reaction, the reaction mixture was cooled to room temperature and poured into 300 ml of 1N-HCl. The resultant precipitate was recovered by filtration and washed with water, followed by drying for 5 hours at 100° C. under reduced pressure and purification by silica gel column chromatography (eluent: chloroform) and recrystallization from a mixture solvent (chloroform/methanol) to obtain 0.20 g of Iridium (III) tris[2-(4-fluoro-5-trifluoromethyl-phenyl) pyridine] (yellow powder) (Yield: 21.5%), which showed a peak emission wavelength $\lambda_{PE}$ in toluene at 25° C. of 466 nm.

EXAMPLE I-19

(Synthesis of Ex. Comp. No. (I-111))

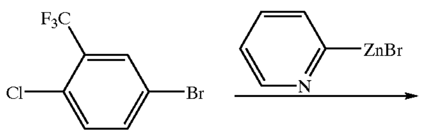

-continued

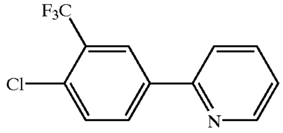

In a 500 ml-three necked flask, 11.8 g (45.5 mM) of 5-bromo-2-chlorobenzotrifluoride and 90 ml of dry tetrahydrofuran (THF) were placed and stirred in a nitrogen gas stream at room temperature. Under stirring, to the mixture, 2.60 g (2.25 mM) of tetrakis(triphenylphosphine) palladium (0) was added, followed by cooling to 13.5–14° C. (inner temperature) on an ice bath in nitrogen gas stream. At that temperature, 90 ml of 0.5 M-THF solution of 2-pyridylzinc bromide was gradually added dropwise to the mixture in nitrogen gas stream, followed by stirring for 3 hours at ca. 20° C.

After the reaction, the reaction mixture was poured into cool water, followed by addition of ethyl acetate to remove the insoluble matter by filtration. The organic layer was washed with water and dried with anhydrous sodium sulfate, followed by distilling-off of the solvent under reduced pressure to obtain a residue. The residue was purified by silica gel column chromatography (eluent: hexane/ethyl acetate=10/1) to obtain 3.70 g of 2-(4-chloro-5-trifluoromethylphenyl)pyridine (pale brown oily product) (Yield: 31.9%).

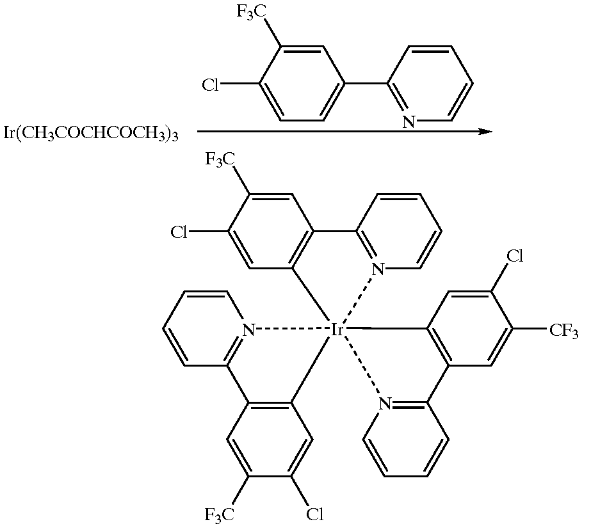

In a 100 ml-four necked flask, 50 ml of glycerol was placed and heat-stirred for 2 hours at 130–140° C. while supplying nitrogen gas therein in the form of bubbles, followed by cooing to 100° C. by standing. To glycerol, 1.29 g (5.01 mM) of 2-(4-chloro-3-trifluoromethylphenyl) pyridine and 0.50 g (1.02 mM) of Iridium (III) acetylacetonate were added, followed by heat-refluxing for 8 hours under stirring in nitrogen gas stream.

After the reaction, the reaction mixture was cooled to room temperature and poured into 300 ml of 1N-HCl. The resultant precipitate was recovered by filtration and washed with water, followed by drying for 5 hours at 100° C. under reduced pressure and purification by silica gel column chromatography (eluent: chloroform) and recrystallization from a mixture solvent (chloroform/hexane) to obtain 0.25 g of Iridium (III) tris[2-(4-chloro-3-trifluoromethylphenyl) pyridine] (yellow powder) (Yield: 25.4%), which showed a peak emission wavelength $\lambda_{PE}$ in toluene at 25° C. of 479 nm.

COMPARATIVE EXAMPLE I-3

(Synthesis of Metal Coordination Compound A)

A metal coordination compound A (iridium (III) tris[2-(4,5-difluoromethylphenyl)pyridine described in Polymer Preprints, 41(1), pp. 770–771 (2000)) was prepared in the same manner as in Example 17 except that 2,4-difluorophenylbronic acid was changed to 3,4-difluorophenylbronic acid.

The metal coordination compound A showed a peak emission wavelength $\lambda_{PE}$ in toluene at 25° C. of 505 nm.

EXAMPLE I-20 AND COMPARATIVE EXAMPLE I-4

Two luminescence devices were prepared and evaluated in the same manner as in Examples I-1 to I-10 except that the metal coordination compound was changed to one (Ex. Comp. No. (122)) prepared in Example I-18 (for Example I-20) and the metal coordination compound A prepared in Comparative Example 3 (for Comparative Example 4), respectively.

The results are shown in Table 18 below.

TABLE 18

| Ex. No. | Ex. Comp. No. | Luminance half-life (Hr) |
|---|---|---|
| I-20 | (I-122) | 630 |
| Comp. Ex. I-4 | Metal coordination compound A | 310 |

As apparent from Table 18, the luminescence device using the metal coordination compound of formula (1) according to the present invention exhibited a luminance half-life considerably longer than that of the luminescence device using the metal coordination compound A, thus resulting in an EL device excellent in durability (luminance stability).

As described hereinabove, the metal coordination compound of formula (1) according to the present invention provides a higher phosphorescence efficiency and a shorter phosphorescence life and allows control of its emission wavelength by appropriately modifying the substituents X1 to X8, thus being suitable as a luminescent material for EL device.

The result EL device (luminescence device) having an organic layer containing the metal coordination compound of formula (1) exhibits excellent characteristics including a high efficiency luminescence, a high luminance for a long period, and a decreased luminescence deterioration in energized state.

EXAMPLES II-1–II-15

In these examples, metal coordination compounds of formula (1) (Ex. Comp. Nos. (II-10), (II-15), (II-17), (II-21), (II-39), (II-43), (II-46), (II-85), (II-96), (II-122), (II-131), (II-146), (II-163), (II-177) and (II-182) were used in respective luminescence layers for Examples II-1–II-15, respectively.

Each of luminescence devices having a structure shown in FIG. 1B were prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 $mm^2$.

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (20 nm): mixture of CBP: metal coordination compound of formula (2) (95:5 by weight)

Organic layer 3 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

Each of the thus-prepared luminescence devices was taken out of the vacuum chamber and was subjected to a continuous energization test in an atmosphere of dry nitrogen gas stream so as to remove device deterioration factors, such as oxygen and moisture (water content).

The continuous energization test was performed by continuously applying a voltage at a constant current density of 70 $mA/cm^2$ to the luminescence device having the ITO (transparent) electrode (as an anode) and the Al (metal) electrode (as a cathode), followed by measurement of luminance (brightness) with time so as to determine a time (luminance half-life) required for decreasing an initial luminance (60–220 $cd/m^2$) to ½ thereof.

The results are shown in Table 19 appearing hereinafter.

COMPARATIVE EXAMPLE II-1

A comparative luminescence device was prepared and evaluated in the same manner as in Example II-1–II-15 except that the metal coordination compound of formula (2) was changed to Ir-phenylpyridine complex ($Ir(ppy)_3$) shown below.

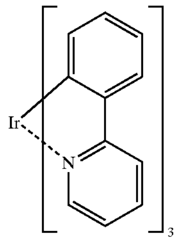

The results are shown in Table 19 below.

TABLE 19

| Ex. No. | Ex. Comp. No. | Luminance half-life (Hr) |
|---|---|---|
| II-1 | (II-10) | 750 |
| II-2 | (II-15) | 950 |
| II-3 | (II-17) | 800 |
| II-4 | (II-21) | 850 |
| II-5 | (II-39) | 900 |
| II-6 | (II-43) | 750 |
| II-7 | (II-46) | 900 |
| II-8 | (II-85) | 500 |
| II-9 | (II-96) | 650 |
| II-10 | (II-122) | 650 |
| II-11 | (II-131) | 600 |
| II-12 | (II-146) | 550 |
| II-13 | (II-163) | 600 |
| II-14 | (II-177) | 450 |
| II-15 | (II-182) | 450 |
| Comp. Ex. II-1 | $Ir(ppy)_3$ | 350 |

As is apparent from Table 19, compared with the conventional luminescence device using $Ir(ppy)_3$, the luminescence devices using the metal coordination compounds of formula (2) according to the present invention provide longer luminance half-lifes, thus resulting in an EL device having a high durability (luminance stability) based on a good stability of the metal coordination compound of formula (2) of the present invention.

EXAMPLES II-16–II-17

In these examples, metal coordination compounds of formula (2) (Ex. Comp. Nos. II-15 and II-17 were used in respective luminescence layers for Examples II-16–II-17, respectively.

Each of luminescence devices having a structure shown in FIG. 1C were prepared in the following manner.

On a glass substrate (transparent substrate 15), a 100 nm-thick film (transparent electrode 14) of ITO (indium tin oxide) was formed by sputtering, followed by patterning to have an (opposing) electrode area of 3 $mm^2$.

On the ITO-formed substrate, three organic layers and two metal electrode layers shown below were successively formed by vacuum (vapor) deposition using resistance heating in a vacuum chamber ($10^{-4}$ Pa).

Organic layer 1 (hole transport layer 13) (40 nm): α-NPD

Organic layer 2 (luminescence layer 12) (20 nm): mixture of CBP: metal coordination compound of formula (2) (93:7 by weight)

Organic layer 3 (exciton diffusion prevention layer 17) (10 nm): BCP

Organic layer 4 (electron transport layer 16) (30 nm): Alq3

Metal electrode layer 1 (metal electrode 11) (15 nm): Al—Li alloy (Li=1.8 wt. %)

Metal electrode layer 2 (metal electrode 11) (100 nm): Al

Separately, each of the metal coordination compounds of formula (2) (Ex. Comp. Nos. (II-15 and (II-17))) for the thus-prepared luminescence devices was subjected to measurement of photoluminescence spectrum in order to evaluate a luminescent characteristic of the metal coordination compounds of formula (2) (Ex. Comp. Nos. (II-15) and (II-17)). Specifically, each of the metal coordination compounds was dissolved in toluene at a concentration of $10^{-4}$ mol/l and subjected to measurement of photo-luminescence spectrum at 25° C. by using excited light (ca. 350 nm) and a spectrophoto-fluorometer ("Model F4500", mfd. by Hitachi K.K.).

The results are shown in Table 20 appearing hereinafter.

The values of photoluminescence spectrum of the metal coordination compounds (Ex. Comp. Nos. (II-15) and (II-17)) were substantially equivalent to those in the luminescence devices under voltage application as shown in Table 20, whereby it was confirmed that luminescence caused by the luminescence device was based on luminescence of the metal coordination compound used.

EL characteristics of the luminescence devices using the metal coordination compounds of formula (1) (Ex. Comp. Nos. (I-1), (I-32) and (I-49)) were measured by using a microammeter ("Model 4140B", mfd. by Hewlett-Packard Co.) for a current density under application of a voltage of 12 volts (current-voltage characteristic), using a spectrophotofluoro-meter ("Model SR1", mfd. by Topcon K.K.) for a peak emission wavelength $\lambda_{PE}$ (luminescence spectrum), and using a luminance meter ("Model BM7", mfd. by Topcon K.K.) for a luminescence efficiency (luminescence luminance). Further, an energy conversion efficiency was obtained according to the following equation:

Energy conversion efficiency (lm/W)=(π×luminescence efficiency (cd/A))/applied voltage (V).

All the above-prepared luminescence devices showed a good rectification characteristic.

The results are shown in Table 20.

COMPARATIVE EXAMPLE II-2

A comparative luminescence device was prepared and evaluated in the same manner as in Example II-16–II-17 except that the metal coordination compound of formula (1) was changed to Ir-phenylpyridine complex ($Ir(ppy)_3$) shown below.

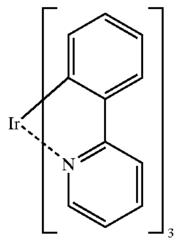

The results ate shown in Table 20 below.

TABLE 20

| Ex. No | Ex. Comp. No. | λPE in toluene (nm) | λPE (nm) | Energy conversion efficiency (lm/W) | Luminescence efficiency (cd/A) | Current density ($mA/cm^2$ at 12 V) | Luminance half-life (Hr) |
|---|---|---|---|---|---|---|---|
| II-16 | (II-15) | 524 | 565 | 0.9 | 7.5 | 70 | 250 |
| II-17 | (II-17) | 554 | 565 | 3.4 | 9.6 | 180 | 300 |
| Comp. Ex. II-2 | $Ir(ppy)_3$ | 510 | 510 | 6.0 | 19.0 | 20 | 150 |

As shown in Table 20, compared with the luminescence device using $Ir(ppy)_3$ (Comparative Example II-2) showing $\lambda_{PE}$=510 nm, the luminescence devices using the metal coordination compound of formula (2) according to the present invention showed longer peak emission wavelengths ($\lambda_{PE}$=565 nm) by 55 nm, thus resulting in smaller relative luminous efficiencies.

Smaller energy conversion efficiencies (0.9–3.4 lm/W) and luminescence efficiencies (7.5–9.6 cd/A) of the luminescence devices of the present invention compared with those (6.0 lm/W and 19.0 cd/A) of the luminescence device using $Ir(ppy)_3$ may be attributable to the smaller relative luminous efficiencies due to the longer peak emission wavelengths, thus not resulting in essentially inferior luminescent characteristics of the luminescence devices using the metal coordination compound of formula (2) of the present invention.

As apparent from the results of the luminance half-lifes of the luminescence devices, compared with the luminescence device using $Ir(ppy)_3$ showing the luminance half-life of 150 hours, the luminescence devices using the metal coordination compounds of formula (2) according to the present invention showed considerably longer luminance half-lifes of 250–300 hours.

EXAMPLE II-18

(Synthesis of Ex. Comp. No. (II-15))

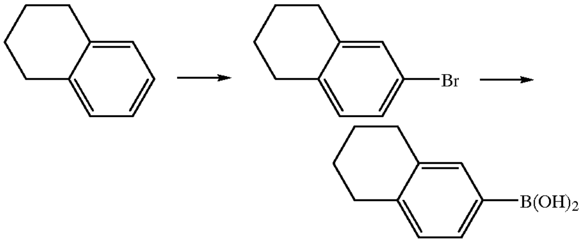

In a 5 liter-three necked flask, 169.5 g (1.28 M) of 1,2,3,4-tetrahydronaphthalene and 3 liters of acetic acid were placed and stirred at room temperature. Under stirring, to the mixture, 650 g (1.67 M) of benzyltrimethylammonium bromide and 244.8 g (1.80 M) of zinc chloride were successively added, followed by stirring for 5.5 hours at 70° C. After the reaction, the reaction mixture was cooled to room temperature and poured into 3 liters of ice water, followed by extraction with methyl t-butyl ether. The organic layer was successively washed with 5% -$NaHSO_3$ aqueous solution, 5% -NaOH aqueous solution and distilled water, followed by distilling-off of the solvent under reduced pressure to obtain 243.2 g of a dark brown liquid. The liquid was subjected to vacuum distillation (distillation under reduced pressure) (boiling point=108–110° C. at 667 Pa) to obtain 130.2 g of 6-bromo-1,2,3,4-tetrahydronaphthalene (Yield: 48.1%).

In a 5 liter-three necked flask, 67.55 g of 6-bromo-1,2,3,4-tetrahydronaphthalene and 1480 ml of dry tetrahydrofuran (THF) were placed and cooled to −70 to −68° C. on a dry ice-acetone bath in a dry nitrogen gas atmosphere. At that temperature, to the mixture, 200 ml of 1.6 M-butyllithium solution in hexane was added dropwise, followed by stirring for 2 hours at −67° C. or below. To borate in 435 ml of dry THF was added dropwise at −70°to −68° C., followed by stirring for 2 hours at −67° C. or below. The reaction mixture was gradually warmed to room temperature and left standing overnight. The resultant reaction mixture was gradually added dropwise to a mixture of 108 ml of HCl and 438 ml of water kept at 10° C. or below, followed by stirring for 1 hour at that temperature. Thereafter, the mixture was subjected to extraction with toluene. The organic layer was washed with water, followed by distilling-off of the solvent under reduced pressure to obtain a residue. The residue was purified by silica gel column chromatography (eluent: toluene/ethyl acetate=2/1) and recrystallized from hexane to obtain 30.4 g of 1,2,3,4-tetrahydronaphthalene-6-boronic acid (Yield: 54.0%).

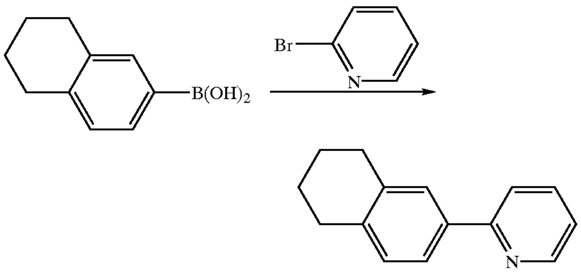

In a 1 liter-three necked flask, 17.8 g (114 mM) of 2-bromopyridine, 20.0 g (127 mM) of 1,2,3,4-tetrahydronaphthalene-6-bronic acid, 160 ml of toluene, 80 ml of ethanol and 160 ml of 2M-sodium carbonate aqueous solution were placed and stirred in a nitrogen gas stream at room temperature. Under stirring, to the mixture, 4.05 g (3.5 mM) of tetrakis (triphenylphosphine) palladium (0) was added, followed by heat-refluxing for 7 hours under stirring in nitrogen gas stream.

After the reaction, the reaction mixture was cooled, followed by extraction with cool water and toluene, and distilling off of the solvent under reduced pressure to obtain a residue. The residue was purified by silica gel column chromatography (eluent: toluene/hexane=2/1) to obtain 9.2 g of 6-(pyridine-2-yl)-1,2,3,4-tetrahydronaphthalene (yellow liquid) (Yield: 38.6%).

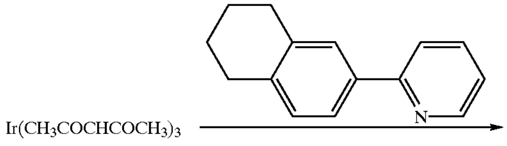

-continued

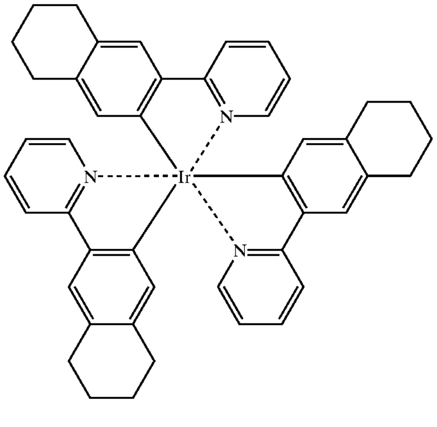

In a 100 ml-four necked flask, 50 ml of glycerol was placed and heat-stirred for 2 hours at 130–140° C. while supplying nitrogen gas therein in the form of bubbles, followed by cooing to 100° C. by standing. To glycerol, 1.30 g (6.21 mM) of 6-(pyridine-2-yl)-1,2,3,4-tetrahydronaphthalene and 0.50 g (1.02 mM) of Iridium (III) acetylacetonate were added, followed by heat-refluxing for 5 hours under stirring in nitrogen gas stream.

After the reaction, the reaction mixture was cooled to room temperature and poured into 100 ml of 1N-HCl. The resultant precipitate was recovered by filtration and washed with water, followed by washing with acetone and purification by silica gel column chromatography (eluent: chloroform) to obtain 0.14 g of Iridium (III) tris[6-(pyridine-2-yl)-1,2,3,4-tetrahydronaphthalene] (orange powder) (Yield: 16.8%).

EXAMPLE II-19

(Synthesis of Ex. Comp. No. (II-17))

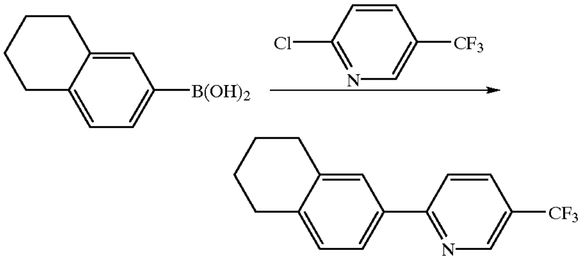

In a 200 ml-four necked flask, 5.16 g (28.4 mM) of 2-chloro-5-trifluoromethyl, 5.00 g (28.4 mM) of 1,2,3,4-tetrahydronaphthalene-6-bronic acid, 25 ml of toluene, 12.5 ml of ethanol and 25 ml of 2M-sodium carbonate aqueous solution were placed and stirred in a nitrogen gas stream at room temperature. Under stirring, to the mixture, 1.02 g (0.88 mM) of tetrakis (triphenylphosphine) palladium (0) was added, followed by heat-refluxing for 3.25 hours under stirring in nitrogen gas stream.

After the reaction, the reaction mixture was cooled, followed by extraction with cool water and toluene, and distilling off of the solvent under reduced pressure to obtain a residue. The residue was purified by silica gel column chromatography (eluent: toluene/hexane=1/1) and alumina column chromatography (eluent: toluene) and recrystallized from methanol to obtain 3.14 g of 6-(5-trifluoromethylpyridine-2-yl)-1,2,3,4-tetrahydronaphthalene (colorless crystal) (Yield: 39.9%).

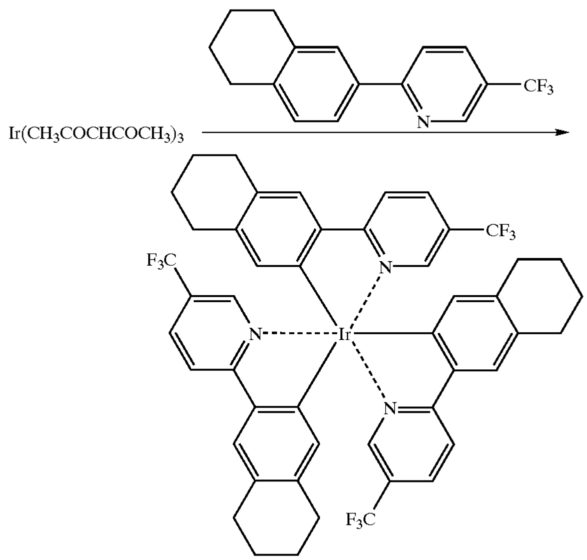

In a 100 ml-four necked flask, 50 ml of glycerol was placed and heat-stirred for 2 hours at 130–140° C. while supplying nitrogen gas therein in the form of bubbles, followed by cooing to 100° C. by standing. To glycerol, 1.72 g (6.20 mM) of 6-(5-trifluoromethylpyridine-2-yl)-1,2,3,4-tetrahydronaphthalene and 0.50 g (1.02 mM) of Iridium (III) acetylacetonate were added, followed by heat-refluxing for 7 hours under stirring in nitrogen gas stream.

After the reaction, the reaction mixture was cooled to room temperature and poured into 100 ml of 1N-HCl. The resultant precipitate was recovered by filtration and washed with water, followed by washing with acetone and purification by silica gel column chromatography (eluent: chloroform) to obtain 0.11 g of Iridium (III) tris[6-(5-trifluoromethylpyridine-2-yl)-1,2,3,4-tetrahydronaphthalene] (orange powder) (Yield: 10.5%).

As described hereinabove, the metal coordination compound of formula (2) according to the present invention provides a higher phosphorescence efficiency and a shorter phosphorescence life and allows control of its emission wavelength by appropriately modifying the alkylene group Y and/or substituents X1 and X2, thus being suitable as a luminescent material for EL device.

The result EL device (luminescence device) having an organic layer containing the metal coordination compound of formula (2) exhibits excellent characteristics including a high efficiency luminescence, a high luminance for a long period, and a decreased luminescence deterioration in energized state.

What is claimed is:

1. A metal coordination compound, which can be used in a luminescence device, represented by the following formula (1):

(1)

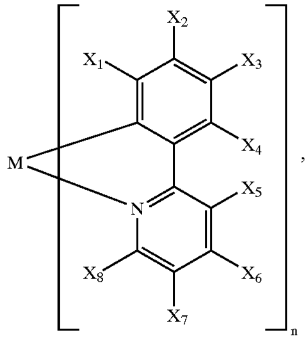
, wherein M is Ir; n is 3; $X_1$, $X_2$, $X_4$, $X_5$, $X_6$, $X_7$, and $X_8$ are H; and $X_3$ is $NO_2$.

2. A luminescence device comprising a metal coordination compound according to claim 1.

3. A metal coordination compound, which can be used in a luminescence device, represented by the following formula (1):

(1)

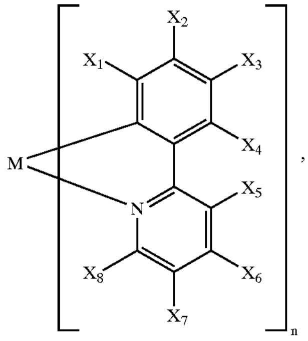
, wherein M is Ir; n is 3; $X_1$, $X_2$, $X_4$, $X_5$, $X_6$, $X_7$, and $X_8$ are H; and $X_3$ is $OCH(CH_3)_2$.

4. A luminescence device comprising a metal coordination compound according to claim 3.

5. A metal coordination compound, which can be used in a luminescence device, represented by the following formula (1):

(1)

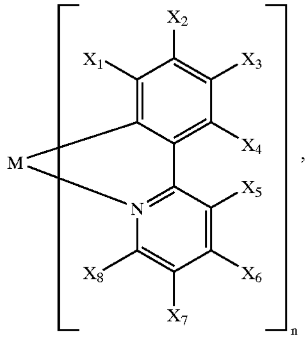
, wherein M is Ir; n is 3; $X_1$, $X_2$, $X_4$, $X_5$, $X_6$, $X_7$, and $X_8$ are H; and $X_3$ is $OC_5H_{11}$.

6. A luminescence device comprising a metal coordination compound according to claim 5.

7. A metal coordination compound, which can be used in a luminescence device, represented by the following formula (1):

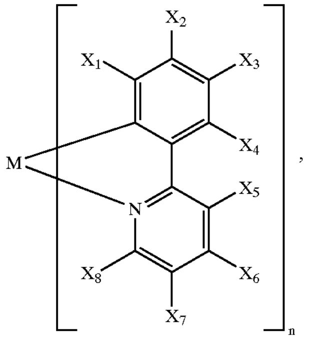

(1)

wherein M is Ir; n is 3; $X_1$, $X_2$, $X_4$, $X_5$, $X_7$, and $X_8$ are H; and $X_3$ is $OCH(CH_3)_2$; and $X_6$ is $OCH_3$.

8. A luminescence device comprising a metal coordination compound according to claim 7.

9. A metal coordination compound which can be used in a luminescence device, represented by the following formula (1):

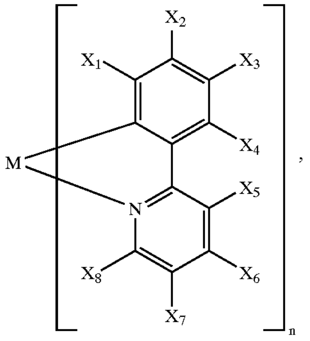

(1)

wherein M is Ir; n is 3; $X_1$, $X_4$, $X_5$, $X_7$, and $X_8$ are H; $X_2$ is $C_2H_5$; and $X_3$ and $X_6$are $OCH_3$.

10. A luminescence device comprising a metal coordination compound according to claim 9.

* * * * *

UNITED STATES PATENT AND TRADEMARK OFFICE
CERTIFICATE OF CORRECTION

PATENT NO. : 6,815,091 B2
DATED : November 9, 2004
INVENTOR(S) : Takao Takiguchi et al.

It is certified that error appears in the above-identified patent and that said Letters Patent is hereby corrected as shown below:

Title page,
Item [56], References Cited, OTHER PUBLICATIONS,
"Peter I. Djurovich et al, "Ir(III) Cyclometalated Complexes as Efficient Phosphoresc nt Emitters in Polymer Blend and Organic LEDs," 41(1) *Polymer Preprints*. 770-771, Mar. 2000." should read -- Peter I. Djurovich et al, "Ir(lll) Cyclometalated Complexes as Efficient Phosphorescent Emitters in Polymer Blend and Organic LEDs," 41(1) *Polymer Preprints*. 770-771, Mar. 2000. -- and "Vladimir V. Grushin et al., "New, Efficient Electroluminescent Materials Based on Organomettalic Ir Complexes," *Chem. Commun.* 1494-1495 (Jul. 23, 2001)." should read -- Vladimir V. Grushin et al., "New, Efficient Electroluminescent Materials Based on Organometallic Ir Complexes," *Chem. Commun.* 1494-1495 (Jul. 23, 2001). --.
Item [57], ABSTRACT,
Line 5, "is," should read -- are, --.

Column 7,
Line 59, "formulas" should read -- formula --.

Column 8,
Line 7, "represents" should read -- P(m) represents --.

Column 11,
Line 32, "reducing" should read -- reduce --.

Column 13,
Table 4, No. (55), "(55) Ir 3 H H H H H $Si(CH_3)_2C_8H_{13}$ H H" should read -- (55) Ir 3 H H H H H $Si(CH_3)_2C_6H_{13}$ H H --; and
Table 6,

| | | | | | | | | | | |
|---|---|---|---|---|---|---|---|---|---|---|
| "(112) | Ir | 3 | H | Cl | $CF_3$ | H | H | H | $CF_3$ | H |
| (113) | Ir | 3 | H | Cl | $CF_3$ | H | H | OCH3 | H | H |
| (114) | Rh | 3 | H | Cl | $CF_3$ | H | H | H | H | H |
| (115) | Rh | 3 | H | Cl | $CF_3$ | H | H | H | $CF_3$ | H |
| (116) | Rh | 3 | H | Cl | $CF_3$ | H | H | CF3 | H | H |
| (117) | Rh | 3 | H | Cl | $CF_3$ | H | H | OCH3 | H | H |
| (118) | Rh | 3 | H | Cl | $CF_3$ | H | H | $C_2H_5$ | H | H |
| (119) | Pd | 2 | H | Cl | $CF_3$ | H | H | H | H | H |
| (120) | Pd | 2 | H | Cl | $CF_3$ | H | H | H | CF3 | CF3" |

should read

UNITED STATES PATENT AND TRADEMARK OFFICE

CERTIFICATE OF CORRECTION

PATENT NO. : 6,815,091 B2
DATED : November 9, 2004
INVENTOR(S) : Takao Takiguchi et al.

It is certified that error appears in the above-identified patent and that said Letters Patent is hereby corrected as shown below:

Column 13 (cont'd),

| | | | | | | | | | |
|---|---|---|---|---|---|---|---|---|---|
| -- (112) | Ir | 3 | H | Cl | $CF_3$ | H | H | H | $CF_3$ | H |
| (113) | Ir | 3 | H | Cl | $CF_3$ | H | H | $OCH_3$ | H | H |
| (114) | Rh | 3 | H | Cl | $CF_3$ | H | H | H | H | H |
| (115) | Rh | 3 | H | Cl | $CF_3$ | H | H | H | $CF_3$ | H |
| (116) | Rh | 3 | H | Cl | $CF_3$ | H | H | $CF_3$ | H | H |
| (117) | Rh | 3 | H | Cl | $CF_3$ | H | H | $OCH_3$ | H | H |
| (118) | Rh | 3 | H | Cl | $CF_3$ | H | H | $C_2H_5$ | H | H |
| (119) | Pd | 2 | H | Cl | $CF_3$ | H | H | H | H | H |
| (120) | Pd | 2 | H | Cl | $CF_3$ | H | H | H | $CF_3$ | $CF_3$ --. |

Column 17,
Table 8, No. (155),
"(155) Ir 3 H H $CF_3$ F H $OCH(CH)_2$ H H"
should read
-- (155) Ir 3 H H $CF_3$ F H $OCH(CH_3)_2$ H H --.

Column 19,
Line 39, "(2-200)" should read -- (2-200)) --.

Column 25,
Line 53, "(I-74)" should read -- (I-74)) --; and
Line 58, "were" should read -- was --.

Column 27,
Line 6, "I-49)" should read -- (1-49)) --; and
Line 10, "were" should read -- was --.

Column 28,
Line 4, "spectrophotofluoro-meter" should read -- spectrophotofluorometer --.

Column 29,
Line 61, "130-140√C." should read -- 130-140°C. --; and
Line 63, "cooing" should read -- cooling --.

Column 31,
Line 2, "cooing" should read -- cooling --; and
Line 12, "100°°C." should read -- 100°C. --.

UNITED STATES PATENT AND TRADEMARK OFFICE
CERTIFICATE OF CORRECTION

PATENT NO. : 6,815,091 B2
DATED : November 9, 2004
INVENTOR(S) : Takao Takiguchi et al.

It is certified that error appears in the above-identified patent and that said Letters Patent is hereby corrected as shown below:

Column 32,
Line 19, "cooing" should read -- cooling --.

Column 33,
Line 25, "cooing" should read -- cooling --.

Column 34,
Line 11, "16.6%)" should read -- 16.6%). --; and
Line 38, "cooing" should read -- cooling -- and "100°°C." should read --100°C. --.

Column 35,
Line 56, "cooing" should read -- cooling --.

Column 38,
Line 25, "II-15 and II-17" should read -- (II-15) and (II-17)) --; and
Line 52, "(II-15 and II-17)))" should read -- (II-15) and (II-17)) --.

Column 39,
Line 11, "spectrophotofluoro-meter" should read -- spectrophotofluorometer --.

Column 42,
Line 21, "cooing" should read -- cooling --; and
Line 53, "tetrahydronaphthalene-6-bronic" should read
-- tetrahydronaphthalene-6-boronic --.

Column 43,
Line 32, "cooing" should read -- cooling --.

UNITED STATES PATENT AND TRADEMARK OFFICE

CERTIFICATE OF CORRECTION

PATENT NO. : 6,815,091 B2 
DATED : November 9, 2004
INVENTOR(S) : Takao Takiguchi et al.

It is certified that error appears in the above-identified patent and that said Letters Patent is hereby corrected as shown below:

Column 46,
Line 18, "$X_6$are" should read -- $X_6$ are --.

Signed and Sealed this

Twenty-second Day of March, 2005

JON W. DUDAS
*Director of the United States Patent and Trademark Office*